US012576201B2

(12) United States Patent
Young et al.

(10) Patent No.: US 12,576,201 B2
(45) Date of Patent: Mar. 17, 2026

(54) METHODS FOR ISOLATING UMBILICAL CORD BLOOD PLASMA PRODUCTS, TISSUE AND CELLULAR EXOSOMES, AND COMPOSITIONS AND METHODS OF USE THEREOF

(71) Applicant: Rutgers, The State University of New Jersey, New Brunswick, NJ (US)

(72) Inventors: Wise Young, New Brunswick, NJ (US); Dongming Sun, Princeton Junction, NJ (US)

(73) Assignee: RUTGERS, THE STATE UNIVERSITY OF NEW JERSEY, New Brunswick, NJ (US)

( * ) Notice: Subject to any disclaimer, the term of this patent is extended or adjusted under 35 U.S.C. 154(b) by 790 days.

(21) Appl. No.: 17/756,016

(22) PCT Filed: Nov. 25, 2020

(86) PCT No.: PCT/US2020/070821
§ 371 (c)(1),
(2) Date: May 13, 2022

(87) PCT Pub. No.: WO2021/108808
PCT Pub. Date: Jun. 3, 2021

(65) Prior Publication Data
US 2022/0395623 A1 Dec. 15, 2022

Related U.S. Application Data

(60) Provisional application No. 62/942,063, filed on Nov. 29, 2019.

(51) Int. Cl.
*A61M 1/36* (2006.01)
*A61K 35/19* (2015.01)
(Continued)

(52) U.S. Cl.
CPC ........... *A61M 1/3693* (2013.01); *A61K 35/19* (2013.01); *A61K 38/363* (2013.01); *C12N 5/0644* (2013.01); *A61M 2202/0427* (2013.01)

(58) Field of Classification Search
None
See application file for complete search history.

(56) References Cited

U.S. PATENT DOCUMENTS 3,347,745 A 10/1967 Rinfret et al.
4,917,799 A 4/1990 Masuda et al.
(Continued)

FOREIGN PATENT DOCUMENTS

CA 3067784 A1 12/2018
CN 108293982 A 7/2018
(Continued)

OTHER PUBLICATIONS

Chantarangkul, et al: "Standardization of the endogenous thrombin potential measurement: how to minimize the effect of residual platelets in stored plasma", British Journal of Haematology, 2004, vol. 124, pp. 355-357.
(Continued)

*Primary Examiner* — Peter Keyworth
(74) *Attorney, Agent, or Firm* — FOX ROTHSCHILD LLP

(57) ABSTRACT

Described herein are novel methods for fractionating and isolating platelets, platelet- and extracellular vesicle-derived growth factors, exosomes, globulins, fibrinogen and albumin, and methods of using the isolated platelets, platelet and extracellular vesicle-derived growth factors, exosomes, globulins, fibrinogen and albumin for regenerating tissue in a subject, treating fibrinogenemia or a clotting deficiency in a subject, treating ischemia and hypoxia, treating dry-eye syndrome, an orthopedic disorder, or a dental disorder in a
(Continued)

subject. Also described herein are growth media for culturing mammalian (e.g., human) cells.

18 Claims, 9 Drawing Sheets

(51) Int. Cl.
    *A61K 38/36*       (2006.01)
    *C12N 5/078*     (2010.01)

(56) References Cited

U.S. PATENT DOCUMENTS

| | | | |
|---|---|---|---|
| 5,258,126 | A | 11/1993 | Pall et al. |
| 6,482,585 | B2 | 11/2002 | Dottori |
| 8,852,938 | B2 | 10/2014 | Sun et al. |
| 9,005,888 | B2 | 4/2015 | Antes et al. |
| 2004/0230051 | A1 | 11/2004 | Freeman et al. |
| 2006/0127375 | A1 | 6/2006 | Livesey et al. |
| 2009/0176708 | A1 | 7/2009 | Turecek et al. |
| 2011/0177488 | A1 | 7/2011 | Natan et al. |
| 2012/0164111 | A1 | 6/2012 | Osther |
| 2012/0244129 | A1 | 9/2012 | Dezawa et al. |
| 2013/0183655 | A1 | 7/2013 | Monroe et al. |
| 2014/0308656 | A1 | 10/2014 | Flower |
| 2015/0329827 | A1 | 11/2015 | Young et al. |
| 2017/0056447 | A1 | 3/2017 | Shim |
| 2017/0198251 | A1 | 7/2017 | Elhofy et al. |
| 2017/0239298 | A1 | 8/2017 | Keith et al. |
| 2017/0296626 | A1 | 10/2017 | Tarnopolsky |
| 2018/0072992 | A1 | 3/2018 | Valamehr et al. |
| 2018/0092348 | A1 | 4/2018 | She et al. |
| 2019/0160103 | A1 | 5/2019 | Garbin |
| 2019/0307686 | A1 | 10/2019 | Ye |

FOREIGN PATENT DOCUMENTS

| | | |
|---|---|---|
| CN | 109431985 A | 3/2019 |
| CN | 109666629 A | 4/2019 |
| CN | 109893543 A | 6/2019 |
| EP | 0627161 A1 | 12/1994 |
| EP | 1000541 B1 | 1/2004 |
| RU | 2643107 C1 | 1/2018 |
| WO | 2004/058323 A2 | 7/2004 |
| WO | 2006/081435 A2 | 8/2006 |
| WO | 2011/140654 A1 | 11/2011 |
| WO | 2013151725 A1 | 10/2013 |
| WO | 2016208675 A1 | 12/2016 |
| WO | 2017/174032 A1 | 10/2017 |
| WO | 2018211487 A1 | 11/2018 |

OTHER PUBLICATIONS

Laurent, et al: "Enrichment of extracellular vesicles using Millipore membrane filters", Dec. 21, 2015, [retrieved on Feb. 8, 2021], Retrieved from the Internet: URL: <https://www.researchsquare.com/article/nprot-4411/v1>, pp. 2-4; DOI: 10.1038/protex.2015.110.

International Search Report and Written Opinion issued Apr. 9, 2021 for International Application No. PCT/US20/70821 (10 pages).

Greenwood et al: "Hydroxyethyl Starch as a Cryoprotective Agent for Human Red Blood Cells", Die Stärke, 1977, No. 10, pp. 343-347.

Arduini, et al: "Addition of L-carnitine to additive solution-suspended red cells stored at 4.degree.c reduces in vitro hemolysis and improves in vivo viability", Transfusion, American Association Of Blood Banks, Bethesda, MD, US, Jan. 1, 1997, vol. 2, No. 37, pp. 166-174, XP002075080, ISSN: 0041-1132, DOI:10.1046/J.1537-2995.1997.37297203519.X.

Cloutier, et al: "An Alternative to Dextran for the Thawing of Cord Blood Units", Transfusion, Jul. 2016, vol. 56, pp. 1786-1791.

Deller, et al: "Glycerol-Free Cryoprerservation of Red Blood Cells Enabled by Ice-Recrystallization-Inhibiting Polymers", DOI: 10.1021/acsbiomaterials.5b00162, ACS Biomater. Sci. Eng., 2015, 1, 789-794.

Farrugia, et al: "Cryopreservation of Red Blood Dells: Effect of Freezing on Red Cell Quality and Residual Lymphocyte Immunogenicity", J. Clin Pathol, 1993: vol. 46: pp. 742-745.

Nickolas Greer: Freezing Under Pressure: A New Method of Cryoprerservation, Cryobiology, 2015, No. 70, pp. 66-70.

Kuroda, et al: "Isolation, culture and evaluation of multilineageÂ-differentiating stress-enduring (Muse) cells", Nature Protocols, Jan. 1, 2013, vol. 8, No. 7, pp. 1391-1415, XP055496476.

Lasser, et al: "Isolation and Characterization of RNA-Containing Exosomes", Journal of Visualized Experiments, Jan. 2012, 59, e3037, pp. 1-6.

Liu, et al: "Hydroxyethyl Starch Interferes with Human Blood Ex Vivo Coagulation, Platelet Function and Sedimentation" , ACTA Anaesthesiologica Taiwanica, Elsevier, Amsterdam, NL, Jun. 1, 2009, vol. 47, No. 2, pp. 71-78, XP026223427.

Mithun, et al: "Human Red Blood Cell Behaviour in Hydroexythyl Starch: Probed by Single Cell Spectroscopy", RSC Advances, Aug. 26, 2020, vol. 10, Iss. 52, pp. 31453-31462.

Mojica-Henshaw, et al: "Serum-converted platelet lysate can substitute for fetal bovine serum in human mesenchymal stromal cell cultures", Cytotherapy, 2013; vol. 15; pp. 1458-1468.

Pogozhykh, et al: "Exploring the Possibility of Cryopreservation of Feline and Canine Erythrocytes by Rapid Freezing with Penetrating and Non-Penetrating Cryoprotectants", PLOS One, DOI:10.1371/journal.pone.0169689, Jan. 10, 2017, p. 1/16.

H. M. Pyle: "Glycerol Preservation of Red Blood Cells", Cryobiology, 1964, vol. I., No. I, pp. 57-60.

Reich-Slotsky, et al: "How We Handled the Dextran Shortage: An Alternative Washing or Dilution Solution for Cord Blood Infusions", Transfusion, Jun. 2015, vol. 55, pp. 1147-1153.

Shiga, et al: "Freeze-Dried Human Platelet-Rich Plasma Retains Activation and Growth Factor Expression after an Eight-Week Preservation Period", Asian Spine Journal, Jun. 30, 2017, vol. 11, No. 3, pp. 329-336.

Soumya, et al: "I-carnitine as a Potential Additive in Blood Storage Solutions: A Study on Erythrocytes", Indian Journal Of Hematology And Blood Transfusion, Springer-Verlag, India, Jul. 11, 2015, vol. 32, No. 3, pp. 328-334, XP036000294, ISSN: 0971-4502, DOI:10.1007/S12288-015-0569-3.

Sputtek, et al: "Cryopreservation of Erythrocytes, Thrombocytes, and Lymphocytes", Transfusion Medicine Hemotherapy, Jan. 1, 2007, vol. 34, No. 4, pp. 262-267, XP093002245, ISSN: 1660-3796, DOI: 10.1159/000104136. Retrieved from the Internet: <https://www.karger.com/Article/Pdf/104 136>.

Sputtek, Andreas, "57. Hydroxyethyl starch 6,8-11, (HES)—A viable alternative for the cryopreservation of human red cells for transfusion and immunization", Cryobiology, Nov. 22, 2011, vol. 63, No. 3, pp. 321-322, XP028597828, ISSN: 0011-2240, DOI:10.1016/J.CRYOBIOL.2011.09.060.

Stella Baar: Albumin and Hydroxy-Ethyl Starch in the Cryopreservation of Red Cells-an In Vitro Study, Transfusion, Mar.-Apr. 1973, vol. 13, No. 2, pp. 73-83.

Wakao, et al: "Multilineage-differentiating stress-enduring (Muse) cells are a primary source of induced pluripotent stem cells in human fibroblasts", Proceedings of the National Academy of Sciences, May 31, 2011, vol. 108, No. 24, pp. 9875-9880, XP055496466.

Westphal, et al: "Hydroxyethyl Starches: Different Products—Different Effects", Anesthesiology, Jul. 1, 2009, vol. 111, pp. 187-202, XP055982538, ISSN: 0003-3022, DOI: 10.1097/ALN.0b013e3181a7ec82.

Tao et al: "Exosomes derived from human platelet-rich plasma prevent apoptosis induced by glucocorticoid- associated endoplasmic reticulum stress in rat osteonecrosis of the femoral head via the Akt/Bad/Bcl-2 signal pathway", Theranostics, Jan. 1, 2017, vol. 7, No. 3, pp. 733-750, XP093124281.

Guo et al: "Exosomes derived from platelet-rich plasma promote the re-epithelization of chronic cutaneous wounds via activation of YAP in a diabetic rat model", Theranostics, Jan. 1, 2017, vol. 7, No. 1, pp. 81-96, XP055615268.

(56)     References Cited

OTHER PUBLICATIONS

Extended Search Report dated Feb. 6, 2024 issued in European Patent Application No. 23207178.7 (9 pages).

Kinoshita et al: "Therapeutic Potential of Adipose-Derived SSEA-3-Positive Muse Cells for Treating Diabetic Skin Ulcers", Stem Cells Translational Medicine, 2015, vol. 4, Issue 2, p. 146-155.

Uchida et al: "Human Muse Cells Reconstruct Neuronal Circuitry in Subacute Lacunar Stroke Model", Stroke, 2017, vol. 48, Issue 2, pp. p. 428-435.

Second Office Action mailed Jun. 12, 2025 issued in Chinese Patent Application No. 2020800829507 (21 pages).

METHODS FOR ISOLATING UMBILICAL CORD BLOOD PLASMA PRODUCTS, TISSUE AND CELLULAR EXOSOMES, AND COMPOSITIONS AND METHODS OF USE THEREOF

CROSS-REFERENCE TO RELATED APPLICATION

This application claims priority to U.S. Provisional Patent Application No. 62/942,063 filed Nov. 29, 2019, which is incorporated herein by reference in its entirety.

FIELD OF THE INVENTION

This invention relates generally to methods for isolating platelets, exosomes, fibrinogen, albumin, globulins, exosomes from umbilical cord blood, peripheral blood, and other biofluids and tissues, and compositions and methods of use thereof, including reagents and methods for culturing mammalian cells and treating diseases and conditions.

BACKGROUND OF THE INVENTION

Umbilical cord blood (UCB) is the baby's blood remaining in the placenta after birth. Made in the placenta, UCB is the richest source of stem cells other than the placenta, more than any adult tissue, including bone marrow. UCB plasma is extracellular fluid of UCB, placenta, and fetus, containing proteins, lipid factors, and exosomes that carry signals between the placenta, uterus, mother, and the baby. About 5% of UCB are collected from >30 million births per year around the world. Most UCB store mononuclear cells that include stem cells.

UCB plasma contains platelets, growth factors (VEGF, G-CSF, EGF and FGF), pro-inflammatory cytokines (IL-2, IL-6, IFN-$\gamma$, TNF-$\alpha$) and other factors that promote survival and growth of human cells (Ehrhart, et al., 2018). EVs are cytoplasmic vesicles that cells release into the extracellular environment. Platelets are small (2-3 $\mu$m) cells that have no nuclei. Made by cells called megakaryocytes, platelets contain growth factors and cytokines packaged into granules. When activated, platelets release these cytokines and growth factors. Human platelets have long been used in growth media for culturing of human cells, as well as treatment of orthopedic and dental problems, and dry-eye syndrome.

Cell culture media require growth factors and cytokines to support and stimulate cell growth and differentiation. Traditionally, cells are grown in fetal bovine serum (FBS), collected from fetal calves in pregnant cows. Human cells grown in FBS take up bovine serum proteins that can trigger immune responses when the cells are transplanted into people. Many people have antibodies against bovine proteins due to widespread consumption of cow's milk. Cells grown in FBS are likely to express bovine serum proteins that activate immune rejection when transplanted. For this reason, the U.S. Food and Drug Administration (FDA) requires "xeno-free" culture media for growing cells intended for transplantation into people.

Platelets are the "first responders" in blood. Made by a bone marrow stem cell called, platelets The most commonly used source of human growth media are human platelet lysates. Platelet lysates are also used to enhance healing of joints and teeth, and to treat conditions such as dry eye syndrome, which affects over 200 million people around the world. Many companies sell human platelet lysates for cell cultures (Klatte-Schulz et. al., Int J Mol Sci, 2018. 19(1).

Most human platelet lysates are prepared from adult human plasma, collected by centrifuging adult human peripheral blood to obtain platelet rich plasma (PRP), mononuclear cells (MNC), and red cell fraction (RCF). Many groups and companies that prepare PRP combined the MNC and PRP. Most platelets end up in the plasma layer but are sticky and may be trapped in the MNC layer or RCF. Most devices that collect platelets from adult blood usually combine MNC and PRP, wasting MNC. Frozen platelets show reduced activation response and impaired signaling (Waters et. al., Transfusion, 2017. 57(12): p. 2845-2857). Standards for platelet lysates have not yet been set (Astori, G., et al., Stem Cell Res Ther, 2016. 7(1): p. 93).

Exosomes are small EVs that are 50-150 nm in diameter. Formed from endosomes created by inward budding of multivesicular bodies (MVB), exosomes possess surface proteins that target specific cells. MVB fuse with the external plasma membrane of cells to release exosomes into extracellular space. Cells send messages through exosomes to each other.

UCB exosomes exert significant beneficial therapeutic and growth effects on cells, as well as anti-immune, regenerative, and other effects on brain, heart, and other organs and tissues. UCB exosomes are the primary means by which placenta communicates with the growing fetus and likely contain transcription factors, mRNA, and $\mu$RNA that stimulate cell growth and differentiation. Placental exosomes have anti-immune effects, giving cells the capability of secreting and expressing molecules that turn off immune cells.

Plasma also contain fibrinogen, clotting factors, as well as albumin and globulins which respectively represent over 50% and 40% of plasma proteins. Plasma fibrinogen and clotting factors can be used to treat patients with fibrinogenemia and clotting deficiencies, and also can be used as a surgical glue when combined with thrombin. Albumin is an important excipient for cell suspensions. Albumin is a carrier molecule for many hormones, cytokines, and drugs. Globulins include immunoglobulins of all types (IgA, IgG, IgM, etc.) and other globulins that can serve as signalling molecules. Fibrinogen is usually isolated by cryoprecipitation while albumin is usually extracted chemically.

Traditional methods of isolating exosomes are inefficient and labor-intensive, requiring ultracentrifugation (>100,000 g) for prolonged periods (>18 hours) in sucrose gradients. The centrifugal forces associated with ultracentrifugation and osmotic forces of sucrose gradients may damage exosomes and releases their contents into the extracellular fluids. Other methods of isolating exosomes include antibody-coated magnetic microbeads and extraction with hydrophobic ingredients.

Thus, there remains a need for more effective and efficient methods for isolating platelets, exosomes, fibrinogen, albumin, globulins, and EVs from tissues, blood, urine, saliva, tears, and other body fluids, to use these components to improve ability of culture media to support growth and differentiation of human and other cells and for treating a variety of disorders.

SUMMARY OF INVENTION

Described herein are novel methods for fractionating and isolating platelets, platelet- and extracellular vesicle-derived growth factors, exosomes, globulins, fibrinogen and albumin, and methods of using the isolated platelets, platelet- and extracellular vesicle-derived growth factors, exosomes, globulins, fibrinogen and albumin for regenerating tissue in a subject, treating fibrinogenemia or a clotting deficiency in a subject, and treating dry-eye syndrome, an orthopedic disorder, or a dental disorder in a subject. Methods described herein include isolating and freeze-drying platelets from platelet-rich-plasma (PRP) to obtain platelet-depleted plasma (PDP) which is an excellent source of growth factors and exosomes for cell cultures. These methods include extracting >90% of exosomes from PDP, and isolating and freeze-drying albumin, globulins, and clotting proteins from the remaining plasma. Methods of activating PDP are also described herein. In the experiments described below, a method of activating PDP as described herein resulted in a cell culture media containing 1% PDP that stimulates growth of Hela cells as well as or better than 10% fetal bovine serum (FBS). Also described herein are growth media for culturing mammalian (e.g., human) cells.

Methods of preparing PDP from UCB, and using concentrated $CaCl_2$ solutions to activate UCB PDP for stimulating cell growth in cell culture are also described herein. Methods of extracting exosomes from UCB PDP include use of ultrasonicated polyethylene glycol (PEG) and cold (e.g., 4° C.) extraction of exosomes. These methods of extracting exosomes are by far the most efficient method of extracting exosomes from biological fluids, recovering over 90% of exosomes from small (1 ml) to large volumes (liters) of fluids. Novel clinical and laboratory uses of UCB PDP and exosomes including improving implantation of fertilized eggs for in vitro fertilization, treatment of neonatal anemia, treatment of brain hypoxia-ischemia, treatment of dry eye syndrome, and many other uses, are described herein.

Accordingly, described herein is a method of isolating platelets and extracellular vesicles (EVs) from a tissue source. The method includes: (i) providing a tissue source of platelets and EVs; (ii) subjecting the tissue source to centrifugation at a first speed followed by centrifugation at a second speed that is higher than the first speed to isolate a platelet-rich plasma (PRP) layer comprising plasma, platelets, and EVs; (iii) filtering the PRP layer with a micropore filter comprising pores that are 0.22 μm in diameter to separate platelets and particles larger than 220 nm in diameter from the PRP layer resulting in isolated platelets attached to the micropore filter and a plasma filtrate consisting essentially of particles smaller than 220 nm in diameter; (iv) freeze-drying the micropore filter in a container under conditions such that growth factors are released from the isolated platelets; and (v) processing the plasma filtrate to isolate EVs smaller than 220 nm in diameter. In embodiments of the method, EVs smaller than 220μ in diameter in step (v) include exosomes that are 50-150μ in diameter. In embodiments of the method, the container is stored at a temperature of –20° C. or lower after step (iv). The method can further include: (vi) adding culture media to the container to thaw and dissolve the growth factors resulting in a growth solution comprising the growth factors; and (vii) withdrawing the growth solution from the container. In embodiments of the method, the tissue source can be, as examples, UCB, umbilical cord, umbilical cord lining, umbilical cord stroma cells (Wharton's jelly), amniotic fluid, amniotic membranes, placenta, and peripheral blood. In embodiments of the method, the micropore filter removes particles larger than 220 nm in diameter. In embodiments of the method, the container can include a closed system.

Also described herein is a method of culturing mammalian cells. The method includes growing a population of mammalian cells in a culture medium comprising the growth solution made according to the methods described herein. In embodiments, the population of mammalian cells are human cells. In embodiments, the tissue source is UCB.

Further described herein is a cell culture medium comprising the growth solution made according to the methods described herein.

Yet further described herein is a method of producing platelet-depleted plasma (PDP). The method includes: (i) obtaining and thawing UCB; (ii) centrifuging the UCB resulting in a platelet-rich-plasma (PRP) fraction; (iii) separating the PRP fraction; and (iv) removing platelets by centrifuging platelet-poor-plasma (PPP) or filtering PDP and cellular debris and extracellular vesicles larger than 220 nm, resulting in a PDP portion that comprises citrate phosphate dextrose (CDP), exosomes, and plasma proteins. In some embodiments, the method further includes activating the PDP portion by adding $CaCl_2$ to the PDP portion to precipitate CPD. In some embodiments, 6 M $CaCl_2$ is added. In some embodiments, 5 M $CaCl_2$ is added to achieve a concentration of 100 mM to precipitate the CPD. In some embodiments, different amounts of $CaCl_2$ are added to precipitate the CPD. Also described herein are methods of obtaining a portion of PDP and activating the portion of PDP by adding $CaCl_2$ (e.g., about 5 M or about 6 M to achieve a concentration of 100 mM $CaCl_2$) to precipitate CPD.

Additionally described herein is a method of isolating one or more of exosomes, globulins, fibrinogen, and albumin from a tissue source. The method includes: (i) providing a tissue source of exosomes, globulins, fibrinogen, and albumin; (ii) subjecting the tissue source to filtration with a micropore filter comprising pores that are 0.22 μm in diameter resulting in a plasma filtrate comprising exosomes, globulins, fibrinogen, albumin, and CPD; (iii) adding the plasma filtrate to a solution comprising polyethylene glycol (PEG) in a first centrifuge tube such that the exosomes partition into PEG bubbles; (iv) cooling the first centrifuge tube to 2° C. to 8° C.; (v) centrifuging the first centrifuge tube such that the exosomes and the PEG form a first pellet, and a first supernatant is formed, the first supernatant comprising albumin, globulins, CPD, and fibrinogen; (vi) transferring the first supernatant to a second centrifuge tube and freezing the first pellet comprising exosomes and PEG for storage, (vii) mixing a precipitating agent with the first supernatant to precipitate CPD; (viii) filtering the precipitating agent and first supernatant mixture to remove the CPD resulting in a second supernatant lacking CPD; (ix) cooling the second supernatant to 2° C. to 8° C. to form a cryoprecipitate comprising fibrinogen; (x) centrifuging the cryoprecipitate in a third centrifuge tube to form a second pellet and a third supernatant, (xii) removing the third supernatant which comprises albumin, and freeze-drying the cryoprecipitate comprising fibrinogen; and (xii) freezing-drying the albumin-containing third supernatant. In embodiments of the method, about 80% to about 95% of the exosomes from the tissue source are isolated. In embodiments of the method, about 90% of the exosomes from the tissue source are isolated. In embodiments of the method, exosomes, fibrinogen, and albumin, are isolated. In embodiments of the method, in step (iv) the first centrifuge tube is cooled under conditions such that globulins in the plasma filtrate crosslink fibrinogen, exosomes partition into PEG, and the precipitating reagent precipitates CPD. In embodiments of the method, in step (v), the first centrifuge tube is centrifuged at a speed in the range of about 1000 to about 5000 revolutions per minute (RPM) for a time period in the range of about 5 minutes to about 30 minutes. In embodiments of the method, the precipitating agent is $CaCl_2$. In embodiments of the method, the tissue source can be, as examples, UCB, umbilical cord, umbilical cord lining, umbilical cord stroma cells (Wharton's jelly), amniotic fluid, amniotic membranes, placenta, and peripheral blood.

Further described herein is a method of producing exosome-rich plasma (ERP). The method includes adding plasma or a saline solution (e.g., PBS) to an exosome pellet obtained according to a method of isolating exosomes as described herein.

Yet further described herein is a method of culturing mammalian cells. The method includes culturing a population of mammalian cells in a culture medium comprising the exosomes and/or the albumin isolated by the methods described herein. In embodiments, the population of mammalian cells are human cells. In embodiments, the tissue source is UCB.

Additionally described herein is a cell culture medium comprising the exosomes, and/or the fibrinogen, and/or the albumin isolated by the methods described herein. A cell culture medium comprising a growth solution comprising exosomes isolated according to the methods described herein or activated PDP produced by the methods described herein is described herein.

Also described herein is a pharmaceutical composition including the platelets and EVs isolated by the methods described herein, or the exosomes, fibrinogen, and/or the albumin isolated by the methods described herein, the PDP produced by the methods described herein, or the ERP produced by the methods described herein.

Further described herein is a method for regenerating a tissue (e.g., cardiovascular tissue central nervous system tissue, ocular tissue, etc.) in a subject (e.g., human subject). The method includes administering to the subject an effective amount of the exosomes isolated by the methods described herein. In embodiments, the subject is a human suffering from at least one disorder such as tissue damage, brain degeneration, central nervous system degeneration, and cardiovascular degeneration.

Still further described herein is a method for treating fibrinogenemia or a clotting deficiency in a subject. The method includes administering to the subject suffering from fibrinogenemia or a clotting deficiency an effective amount of the fibrinogen isolated by the methods described herein.

Yet further described herein is a method for treating dry-eye syndrome, an orthopedic disorder, or a dental disorder in a subject. The method includes administering to a subject suffering from dry-eye syndrome, an orthopedic disorder, or a dental disorder, an effective amount of the platelets isolated by the methods described herein, or the PDP or ERP produced by the methods described herein.

Additionally described herein is a method of culturing mammalian cells. The method includes growing a population of mammalian cells in a culture medium comprising a growth solution comprising exosomes isolated according to the methods described herein or activated PDP produced by the methods described herein.

Also described herein is a method for treating hypoxia, ischemia, or stroke in a subject. The method includes administering to a subject suffering from hypoxia, ischemia, or stroke exosomes isolated according to the methods described herein or PDP produced by the methods described herein.

Further described herein is a method for stimulating uterine vascularization in a subject in need thereof (e.g., a human female). The method includes administering to the subject's uterine cavity PDP produced by the methods described herein or ERP produced by the methods described herein. In embodiments, a composition including the PDP or the ERP can be administered to the subject.

To aid in understanding the detailed description of the compositions and methods according to the disclosure, a few express definitions are provided to facilitate an unambiguous disclosure of the various aspects of the disclosure. Unless otherwise defined, all technical and scientific terms used herein have the same meaning as commonly understood by one of ordinary skill in the art to which this disclosure belongs.

As used in this specification and the appended claims, the singular forms "a," "an," and "the" include plural reference unless the context clearly dictates otherwise. The terms "including," "comprising," "containing," or "having" and variations thereof are meant to encompass the items listed thereafter and equivalents thereof as well as additional subject matter unless otherwise noted.

The phrases "in one embodiment," "in various embodiments," "in some embodiments," and the like are used repeatedly. Such phrases do not necessarily refer to the same embodiment, but they may unless the context dictates otherwise.

The terms "and/or" or "/" means any one of the items, any combination of the items, or all of the items with which this term is associated.

The term "about" can refer to a variation of ±5%, ±10%, ±20%, or ±25% of the value specified. For example, "about 50" percent can in some embodiments carry a variation from 45 to 55 percent. For integer ranges, the term "about" can include one or two integers greater than and/or less than a recited integer. Unless indicated otherwise herein, the term "about" is intended to include values, e.g., weight percents, proximate to the recited range that are equivalent in terms of the functionality of the individual ingredient, the composition, or the embodiment.

As used herein, the term "each," when used in reference to a collection of items, is intended to identify an individual item in the collection but does not necessarily refer to every item in the collection. Exceptions can occur if explicit disclosure or context clearly dictates otherwise.

The terms "platelet-depleted plasma" and "PDP" mean plasma from which platelets have been removed in part or completely. The terms "activated PDP" and "aPDP" mean platelet depleted plasma that have been treated with calcium ions to precipitate citrate-phosphate-dextrose (CPD) and other chemicals that bind and lower calcium ion concentrations to levels sufficient to prevent blood clotting, restoring calcium ionic activity to a level sufficient to support cell growth.

As used herein, the terms "red cell fraction" and "RCF" mean the fraction of centrifuged peripheral blood or umbilical cord blood that contains the red blood cells.

The terms "platelet rich plasma" and "PRP" mean plasma that contains platelets. The plasma should contain as much or more platelets than normal blood or umbilical cord blood (UCB).

As used herein, the terms "ERP" and "exosome rich plasma" mean plasma that contains exosomes in a concentration that is greater than normal blood. ERP differs from PRP in that ERP contains exosomes and little or no platelets while PRP contains both platelets and exosomes.

As used herein, the term "purified," means that a compound or entity (such as cells) is separated from other compounds or entities. A compound or entity (e.g., protein, peptide, cell) may be partially purified, substantially purified, or pure.

A compound or entity is considered pure when it is removed from substantially all other compounds or entities, i.e. preferably at least about 90%.

The term "isolated" and the phrase "biologically pure" refer to material which is substantially or essentially free from components which normally accompany it as found in its native state.

The terms "patient," "subject" and "individual" are used interchangeably herein, and mean a mammalian (e.g. human) subject to be treated, diagnosed, and/or to obtain a biological sample from. The subject can be affected with, for example, anemia, hypoxia-ischemia, stroke, hypo-endometria, an autoimmune condition (e.g., multiple sclerosis, systemic lupus erythematosus, rheumatic arthritis, psoriatic arthritis), etc.

As used herein, the term "therapeutic agent" is meant to encompass any molecule, cell, chemical entity, composition, drug, or biological agent capable of curing, healing, alleviating, relieving, altering, remedying, ameliorating, improving or affecting a disease, the symptoms of disease, or the predisposition toward disease. The term "therapeutic agent" includes polypeptides, peptides, cells, organic or inorganic molecules, natural or synthetic compounds and the like.

As used herein, the terms "treatment" and "therapy" mean application or administration of a therapeutic agent to a patient, or application or administration of the therapeutic agent to an isolated tissue from a patient, who has a disease or condition, a symptom, or a predisposition toward a disease or condition, with the purpose to cure, heal, alleviate, relieve, alter, remedy, ameliorate, improve, eliminate, or otherwise affect the disease or condition, the symptoms of the disease or condition, or predisposition toward the disease or condition. Treatments include pharmaceutical compositions that can inhibit, decrease, reduce, or eliminate adverse (e.g., physical) symptoms, disorders, illnesses, diseases or complications caused by or associated with a disease (e.g., anemia, hypoxia-ischemia, stroke, dry-eye syndrome, fibrinogenemia or clotting deficiency, orthopedic disorder, dental disorder, hypo-endometria, multiple sclerosis, systemic lupus erythematosus, rheumatic arthritis, psoriatic arthritis, etc.).

The phrases "therapeutically effective amount" and "effective dosage" mean an amount sufficient to produce a therapeutically (e.g., clinically) desirable result; for example, the result can be stimulating vascularization and blood flow (e.g., stimulating endometrial growth), improving neurological recovery from hypoxia and/or ischemia (e.g., hypoxic-ischemic encephalopathy) in a subject (e.g., mammals including humans), suppressing the immune system in a subject suffering from an autoimmune condition, treating fibrinogenemia or a clotting deficiency in a subject, treating dry-eye syndrome in a subject, treating an orthopedic disorder in a subject, treating a dental disorder in a subject, etc.

As used herein, "spinal cord injury" and "SCI" refer to damage to the spinal cord resulting from trauma, including prolonged compression (>20 minutes), contusion (>0.5 m/sec), and partial section or transection, as well as non-traumatic causes such as inflammation, infection, edema (swelling), toxin(s), hypoxia-ischemia resulting from cardiac arrest or aortic aneurism, spinal canal stenosis (narrowing), demyelination, and tumor infiltration. Compression of the spinal cord results from indentation of the spinal cord by herniated disc, displaced bone, growing tumor, and adhesions. Contusion is rapid indentation of the spinal cord at speeds close to or exceeding 0.5 m/sec, causing rapid displacement of tissue to stretch and break cellular processes including dendrites and axons. Partial sections or transections result from penetrating wound(s) that cut into the spinal cord. Inflammation can be from an autoimmune inflammatory disease such as lupus erythematosus, entry of inflammatory cells (white blood cells) or infectious cells (bacterial, fungus, parasites, viruses), infections of the meninges (meningitis), loss of cerebrospinal fluid (CSF) flow due to adhesions or leakage. Toxins from many sources, including bacteria and fungi, can damage the spinal cord. Infections include tuberculosis, rabies, viruses, and fungi. Demyelination may result from toxins and autoimmune attack of oligodendroglia. Tumor infiltration can occur from metastatic or intrinsic tumors of the central nervous system. When applied to spinal cord injury, the term "acute" means an early period during which injury or other event is occurring and the term "chronic" means a continuing stable state after injury.

As used herein, "hypoxic ischemia" of the brain and spinal cord means reduced oxygenation of and blood flow to the brain. The most frequent causes of hypoxia and ischemia to the brain or spinal cord are carotid artery occlusion, cardiac arrest, aortic occlusion by a dissecting aneurism or trauma. In neonates, hypoxic ischemia occur from umbilical cord strangulating the neck during delivery and prolonged passage in the birth canal.

As used herein, "stroke" refers to damage to the brain resulting from occlusion of blood vessels within and leading to the brain, hemorrhage of these blood vessels, or embolism of the vessels. For example, cardiac arrest would not be considered a "stroke" but is hypoxic-ischemia resulting from the heart no longer pumping blood. The incidence of stroke is variable and range from 30 to 120 per 100,000 per year in people who are 35-44 years old and 670 to 970 per 100,000 in people who are 65-70. In the U.S., about 800,000 people have first time or recurrent strokes per year and about 3% (about 7 million) of the adult population have had strokes (https://www.ncbinlm.nih.gov/pmc/articles/PMC3250269/). Over 80 million people around the world have long term neurological disabilities associated with stroke.

As used herein, "macular degeneration" means degeneration of retinal neurons, called ganglionic cells. The most common category is age-related macular degeneration (AMD), which is the leading cause of blindness around the world, affecting over 200 million people worldwide. In the United States, about 11 million people have macular degeneration. Other causes of macular degeneration include macular ischemia, which includes diabetic related eye conditions and other causes of ganglionic cell loss. Therapies for macular ischemia include prevention of macular degeneration, regeneration of the optic nerve, or replacement of retinal ganglionic neurons that have degenerated. Note that other therapies include replacement of the pigmented retinal epithelium that nourishes the retinal visual cells. Umbilical cord blood plasma and exosomes may stimulate retinal ganglionic growth.

As used herein, the term "dry eye syndrome" and "DES" mean a condition where tears do not provide sufficient or appropriate quality lubrication of the eyes. DES is associated with many inflammatory conditions, such as Sjogren's syndrome, rheumatoid arthritis, and collagen vascular diseases. Most therapies of DES use artificial replacement tears, surgery to keep tears from flowing out, and the immunosuppressant cyclosporin A to suppress immune responses. Several components of UCB, including umbilical cord blood exosomes and PDP may be beneficial for DES.

As used herein, the term "endometria atrophy" refers to thinning of the endometria layer in the uterus. Normally, the endometrial is about a cm thick. However, in older women (>35 years old), post-menopausal women, and women with ovarian dysfunction, prolonged oral contraception, and tamoxifen use, endometrial thickness is <5 mm thick. In women with endometria atrophy, in vitro fertilization and implantation of fertilized ova often fail. Umbilical cord blood exosomes contain vascular factors, including vascular endothelial growth factor (VEGF) that stimulate vasculo-genesis and endometria growth to restore endometrial thick-ness for in vitro fertilization (IVF).

The foregoing summary is not intended to define every aspect of the disclosure, and additional aspects are described in other sections, such as the following detailed description. The entire document is intended to be related as a unified disclosure, and it should be understood that all combinations of features described herein are contemplated, even if the combination of features are not found together in the same sentence, or paragraph, or section of this document. Other features and advantages of the invention will become appar-ent from the following detailed description. It should be understood, however, that the detailed description and the specific examples, while indicating specific embodiments of the disclosure, are given by way of illustration only, because various changes and modifications within the spirit and scope of the disclosure will become apparent to those skilled in the art from this detailed description.

DETAILED DESCRIPTION OF THE INVENTION

Figure 1:
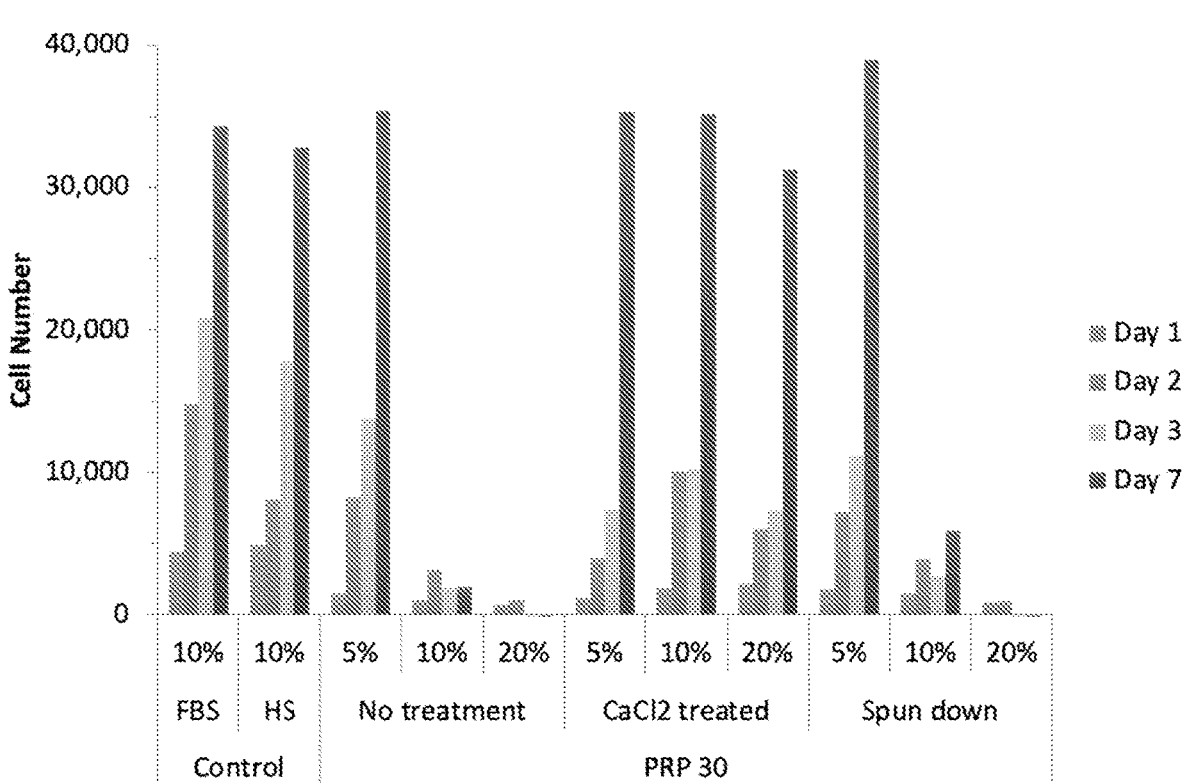
FIG. 1 is a graph showing the effect of adding UCB platelet rich plasma (PRP) without and with $CaCl_2$ activation on HeLA cells. The left-hand side of the graph shows the effects of 10% fetal bovine serum (FBS) and 10% adult human serum (HS). If PRP is applied to the culture media without $CaCl_2$ treatment, the effect on cell number at 5% concentration is similar to 10% FBS or 10% HS. However, higher concentrations of 10% or 20% PRP suppressed the cell growth. After treatment with $CaCl_2$, adding 5%, 10%, and 20% PRP (sample PRP 30) had similar growth effects at 7 days as 10% FBS or 10% HS. The addition of the $CaCl_2$ to PRP resulted in precipitation of the platelets. On the far left, after centrifugation of the $CaCl_2$ treated PRP (spun down) to bring down the precipitates, growth of the cells returned to the effects seen without the $CaCl_2$ treatment. This data indicate remarkably potent (tenfold) growth stimulation by 1% PRP added to culture medium, a growth effect that is equal to 10% FBS or 10% HS. However, the observation that higher 10% and 20% concentrations of PRP did not stimulate as much growth as 1% PRP, 10% FBS, or 10% HS, suggests that the PRP contain material that was suppressing HeLA cell growth. This material is likely to be citrate-phosphate-dextrose (CPD), which binds calcium ions, reducing extracellular calcium ionic activity below the lev-els that are necessary to allow cell growth. It is interesting that centrifugation of the precipitate (presumably CPD) returned the growth effect to levels before adding the $CaCl_2$. It is possible that the addition of $CaCl_2$ activated platelets and released growth factors from the platelets and contribute to the cell growth.

This disclosure describes a method of isolating platelet-rich-plasma (PRP) from UCB and peripheral blood.

This disclosure describes a method of isolating, activating, and cryopreserving as from UCB and peripheral blood.

This disclosure describes methods to produce platelet-depleted plasma (PDP) from UCB and "activating" UCB PDP to stimulate cell growth in culture.

This disclosure also describes novel methods of very efficiently isolating exosomes from UCB, other biological fluids, including peripheral blood, cerebrospinal fluid (CSF), and urine, as cell as conditioned media from cell cultures.

This disclosure also describes efficient methods of isolating globulins, albumin and fibrinogen from UCB and peripheral blood.

This disclosure also describes cell culture medium and methods of culturing mammalian (e.g., human) cells using freeze-dried platelets, PDP, exosomes.

This disclosure also describes pharmaceutical compositions including the platelets, exosomes, albumin and fibrinogen isolated by the methods described herein.

This disclosure also describes methods for regenerating a tissue in a subject, for treating fibrinogenemia or a clotting deficiency in a subject, and for treating dry-eye syndrome, an orthopedic disorder, or a dental disorder in a subject.

The following section defines components of plasma relevant to the methods, kits, and compositions described herein.

UCB Plasma Components

Plasma is the clear extracellular fluid of UCB and peripheral blood. Plasma differs from serum, which is the supernatant of clotted blood. To make serum, the blood is allowed to clot, resulting in the breakdown of blood cells. When the clot is centrifuged down, the remaining supernatant is a straw-colored fluid that contains extracellular and intracellular fluids. In contrast, plasma is the supernatant of anti-coagulated blood, prevented from clotting by chemicals such as citrate-phosphate-dextrose (CPD) or heparin and contains only extracellular contents, including the anti-coagulant, but not intracellular contents of the clotted cells.

Depending on hematocrit of the blood, the volume of UCB plasma ranges from 40-60% of blood volume. When separated by centrifugation, plasma contains platelets. Platelets are relatively light and tend to fractionate with plasma after centrifugation but because platelets are sticky, as much as 50% of the platelets may be trapped in RCF or MNC layers. If the centrifugation is staged so that blood is spun at a relative slow speed (100×g) and the mixture is agitated to transfer platelets from one layer to the next, a second centrifugation at a higher speed may result in as much as 80% of platelets localizing to the plasma layer.

Platelets

Plasma that has high concentrations of platelets is called platelet-rich-plasma (PRP). Platelets are 2-3 μm in diameter and are filled with granules of growth factors and cytokines that are released when the platelet is activated. Adult blood has about 200,000 platelets per ml. UCB platelet counts are variable but should approach platelet counts of adult blood. Platelet production is regulated by thrombopoietin. Each megakaryocyte makes about 1000-3000 platelets in its lifetime. An average of 100 billion ($10^{11}$) platelets are made every day. Platelets are the "first responders" to injury. Tissue injury causes platelets to stick to blood vessels, activate and release factors that attract stem cells and inflammatory/immune cells. Platelet lysates are used as a source of growth factors of cell culture growth.

Exosomes

Exosomes are released by placental and UCB cells, particularly monocytes, macrophages, and platelets. They range from 30 nm to 150 nm in diameter. Larger EV's usually contain waste from cells. Exosomes form inside the multi-vesicular bodies (MVB) inside cells. Exosomes carry "cargoes" that include μRNA and transcription factors that signal to the uterus and the fetus. Cells communicate with each other through exosomes. Exosomes differ from other EVs in having endosomal sorting complexes for transport (ESCRT) or soluble N-ethylmaleimide sensitive factor (NSF) attachment protein receptor (SNARE) system to dock onto cells. When exosomes dock on these receptors, they upload their contents into the cells. Exosome membranes also contain cholesterol, sphingomyelin, ceramide, and phosphatidyl-serine, which distinguish them from liposomes. Exosomes may include beneficial and harmful factors, including signals to cause apoptosis of cells.

Plasma Proteins

Four classes of proteins dominate umbilical cord blood plasma. The first is albumin, which accounts for more than half of plasma protein (55.2%, 2.8-4.5 g/dl) with a molecular weight of 69 KD. The second is fibrinogen, the precursor protein to fibrin that forms clots. In addition, plasma contains pro-thrombin, the precursor protein to thrombin that catalyzes clots. The third are globulins, i.e., alpha-1 globulins (5.3%, including alpha1-anti-trypsin, TBG, transcortin, etc.), alpha-2 globulins (8.6%, including hepatoglobulins, seruloplasmin, alpha2-macroglobulin, etc.), beta globulins (13.4%, including Beta1-transferrin, beta lipoprotein, etc.), and gamma-globulins (11.0%, including antibodies IgA, IgG, and IgM). The total concentration of serum globulins is about 0.42 g/dl. Fourth, fibrinogen (6.5%) is the clotting protein of blood. With a molecular weight of 340 KD, fibronogen has 6 polypeptide chains that is converted to fibrin by thrombin and other clotting fibers.

Methods to Isolate and Cryopreserve Platelets from Blood

In embodiments of isolating platelets, the first stage centrifugation speed should be low, generating about 100 g for 10-20 minutes. The speed is adjusted to achieve the minimum duration of centrifugation needed to separate RCF from MNC. The red color of RCF clearly distinguished RCF and MNC from the "buffy coat layer" of MNC. The RCF is removed from the bottom of the tube. The remaining MNC and PRP is sometimes called white blood (WB). It is agitated to loosen platelets adhering MNC to enter the PRP.

In embodiments of isolating platelets, the second stage centrifugation is at a higher speed to generate 500-1000×g for 20-30 minutes to separate MNC and PRP. MNC can be distinguished from PRP by light scattering of MNC. The PRP is removed from the top of the centrifuge to concentrate or isolate platelets. To concentrate platelets, the PRP is placed in a separate centrifuge tube and centrifuged to at high speeds to achieve 1000-3000 g's, pelletting the platelets to the bottom of the tube. Removing the supernatant leaves a more concentration suspension of platelets at the bottom of the tube.

Filtration can be used to isolate platelets from PRP. If the sample has cellular debris, EV's, and exosomes in PRP, the filtration can be done in stages. Prefiltering with a 1 μm filter will help clean up the mixture before using the micropore filter with 0.22μ pores. Otherwise, PRP contains the mixture can be directly passed through a micropore filter with 0.22μ pores. The micropore filter will capture all platelets, in addition to bacteria and most viruses. Platelets are 2-3 μm in diameter and pass through the filter.

In the methods described herein, the term "processing" means adding the plasma filtrate to a PEG-containing solution to isolate exosomes. Such a method can further include the steps of adding culture media to the container to thaw and dissolve the growth factors resulting in a growth solution including the growth factors, and withdrawing the growth solution from the container. This growth solution can then be used in the cell culture media and methods described in more detail below.

A method of isolating one or more of: exosomes, globulins, fibrinogen, and albumin from a tissue source includes: providing a tissue source of exosomes, globulins, fibrinogen, and albumin; subjecting the tissue source to filtration with a micropore filter having pores that are 0.22 μm in diameter resulting in a plasma filtrate that includes exosomes, globulins, fibrinogen, albumin, and CPD; adding the plasma filtrate to a solution that includes PEG (e.g., ultrasonicated PEG) in a first centrifuge tube such that the exosomes partition into PEG bubbles; cooling the first centrifuge tube to 2° C. to 8° C. (e.g., about 4° C.); centrifuging the first centrifuge tube such that the exosomes and the PEG form a first pellet, and a first supernatant is formed, the first supernatant including albumin, globulins, CPD, and fibrinogen; transferring the first supernatant to a second centrifuge tube and freezing the first pellet that includes exosomes and PEG for storage, mixing a precipitating agent with the first supernatant to precipitate CPD; filtering the precipitating agent and first supernatant mixture to remove the CPD resulting in a second supernatant lacking CPD; cooling the second supernatant to 2° to 8° C. (e.g., about 4° C.) to form a cryoprecipitate including fibrinogen; centrifuging the cryoprecipitate in a third centrifuge tube to form a second pellet and a third supernatant, removing the third supernatant which includes albumin, and freeze-drying the cryoprecipitate including fibrinogen; and freezing-drying the albumin-containing third supernatant. In this method, after exosome isolation by PEG, the left over PPP is used to isolate albumin, fibrinogen, globulin, and clotting factors.

In the methods of isolating one or more of: exosomes, globulins, fibrinogen, and albumin from a tissue source, any suitable tissue source (e.g., UCB) that includes one or more of: exosomes, globulins, fibrinogen, and albumin can be used. In a typical method, the tissue source is filtered (subjected to filtration) with a micropore filter having pores that are 0.22 μm in diameter. Any suitable filter that can separate particles larger than approximately 220 nm in diameter from the tissue source can be used in embodiments. In embodiments, the solution including PEG can be a solution of 10% PEG. In some embodiments, ultrasonicated PEG is used. Ultrasonicated PEG can be produced using known methods or commercially obtained. When centrifuging the first centrifuge tube such that the exosomes and the PEG form a first pellet and a first supernatant is formed, the centrifuge speed is typically about 3000 g (typically 1000 to about 5000 revolutions per minute (RPM)) and centrifugation is performed for about 20 minutes (typically in the range of 5 to 30 minutes). In embodiments, after this centrifugation, the first supernatant includes albumin, globulins, CPD and fibrinogen. In the method, the precipitating agent is typically CaCl₂, but any suitable precipitating agent can be used. Once the exosomes, fibrinogen, and albumin are isolated, they are each stored under suitable conditions.

The disclosed methods can be used to isolate platelets, EVs, exosomes, globulins, fibrinogen, and albumin from UCB. Umbilical cord blood is an attractive source of platelets, EVs, exosomes, globulins, fibrinogen, albumin, as well as PRP, PDP, aPDP, etc.

The disclosed methods are also applicable for isolating platelets, EVs, exosomes, globulins, fibrinogen, and albumin from other tissues besides UCB. Non-limiting examples of such sources include peripheral blood, umbilical cord, umbilical cord stroma cells (Wharton's jelly), amniotic fluid which may include amniotic cells, placenta, umbilical cord lining, urine and menstrual blood.

Plasma products are produced from platelet-rich-plasma (PRP) produced by separating out red blood cells (RBC) or red cell fraction (RCF) from mononuclear cells (MNC) and PRP (also called White Blood). The standard method of separating UCB and adult blood into red blood cells (RBC) from MNC and PRP (called White Blood) is to centrifuge blood at a slow speed to segregate RCF from WB and then centrifugation at a higher speed to segregate MNC from PRP.

The following examples indicate methods of isolating PRP with two types of centrifuges:

1. UCB can be centrifuged in a horizontal rotor with multiple centrifuge tubes in swinging brackets. Red blood cells (RBC) will settle at the bottom of the tube to form the red cell fraction (RCF) after 30 minutes. The initial centrifugation is done at a low speed, typically at 900 rpm (11 cm rotor radius) to generate about 100×g to separate the red cell fraction (RCF) from the MNC and PRP or WB. The RCF is removed from the bottom of the tube and the remaining MNC and PRP are agitated so that any platelets stuck in the MNC layer would float into the plasma. Centrifuging at 2000-2500 rpm, which yields 492-769×g for 20-30 minutes, should separate MNC and PRP layers, which can be separately removed.

2. UCB can be centrifuged in a spinning cylinder centrifuge. Red blood cells (RBC) will form an outer RCF layer against the inner cylinder surface, the MNC the middle layer, and PRP the innermost central area of the cylinder. An ascending piston in the cylinder pushes the spinning mixture up while a central tube collects the cells. The spinning cylinder can reverse directions to agitate cells during spinning to detach adherent platelets so that they can migrate to the plasma. PRP is first to come out. A light scatter sensor can be used to determine when nucleated cells are coming out and switch collection containers to collect the MNC. Finally, the RCF can be readily detected from the red hemoglobin color of the RBC.

In practice, sequential two-stage centrifugation with agitation between stages yields MNC with <5% hematocrit and PRP with >80% of platelets. RFC and MNC are separately cryopreserved. PRP can be efficiently and quickly separated into several components that have important therapeutic effects, specifically freeze-derived platelets (FDP), platelet-depleted plasma (PDP), exosomes, exosome-rich plasma (ERP), as well as plasma globulins, albumin, and clotting proteins. With modification, the centrifugation method can be used to separate tissue components and other biological fluids into processable components.

Filtration of PRP with a micropore filter with 0.22 μm pores will extract 99% of platelets from PRP, as well as most bacteria and viruses. The resulting sterile filtrate is called platelet-depleted-plasma (PDP). Depending on the source, the tissue solution or PRP may need centrifugation or pre-filtering to avoid clogging the micropore filters. While filtration has long been used to isolate platelets (cells and other biological components), the novel aspect of the method described is that the platelets are freeze-dried (lyophilized) to break down their granules to soluble proteins.

Filters containing the freeze-dried platelet powder can be stored in capped sterile micropore filters, sealed in plastic, and stored for many years at −20° C. When needed to stimulate cell growth in culture, the filters would be culture media can be injected through the filters, which would dissolve the freeze-dried granule chemicals and also sterilize the filtrate. The amount of platelets on each filter can be estimated from the platelet concentration and PRP volume filtered.

Figure 5:
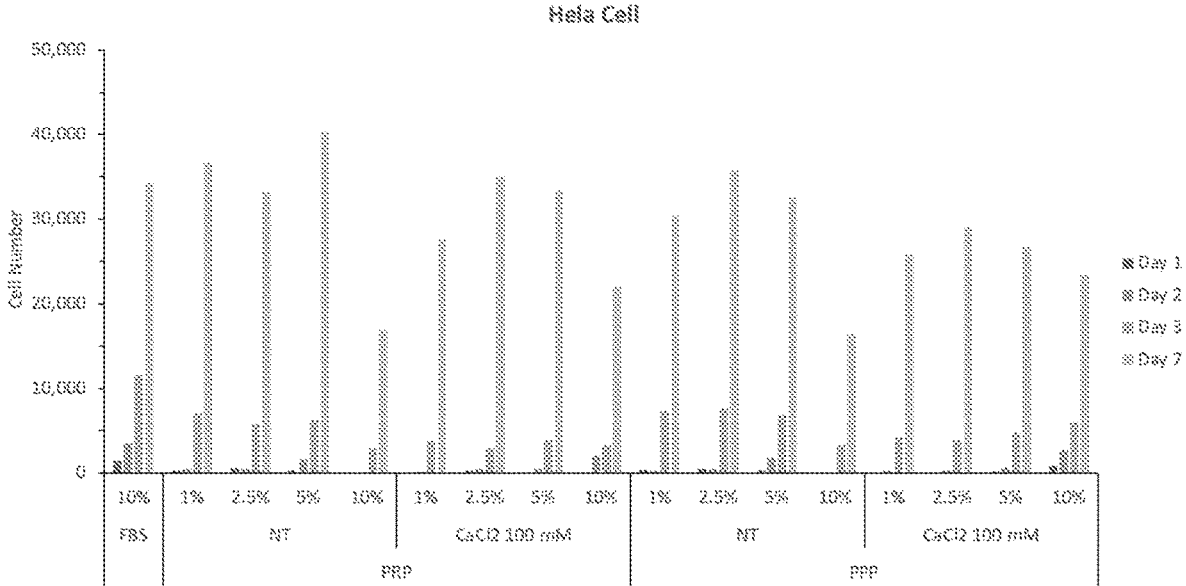
FIG. 5 is a graph showing the effects of $CaCl_2$ activation of platelet-rich-plasma (PRP) and platelet-poor-plasma (PPP) on HeLa cell growth. PPP refers to plasma centrifuged to remove platelets. PRP does not require activation when used in lower concentrations (1-5%) but 10% PRP inhibits growth. In the presence of platelets, i.e. PRP at 1%, 2.5%, and 5.0% concentrations increases cell counts and only 10% PRP seems to be inhibited. When 100 mM $CaCl_2$ is added, it improve the growth rates. In the absence of platelets, i.e. 10% PPP does not stimulate as much cell growth without $CaCl_2$ activation.

The filtrate resulting from micropore aeration of PRP is called platelet-depleted plasma (PDP). In other embodiments, centrifugation can be used to isolate the platelets. Under high speed centrifugation (>2500×g) of PRP, platelets will form a pellet. Because centrifugation may not pellet all the platelets, the supernatant of centrifuged PRP is platelet-poor-plasma (PPP), rather than PDP, as in FIG. 5. The pellet is be freeze dried or stored in a sealed vial.

Passing a phosphate-buffered saline or cell culture media through a micropore filter with freeze-dried platelets will extract soluble proteins, including growth factors and cytokines. Use of a 0.22μ micropore filter has several advantages. First, sterile micropore filters are widely available and are inexpensive. Second, the 0.22μ micropore filter will eliminate most cellular debris and capture EV that are larger than 0.22 μm. Third, freeze-dried micropore filters with the platelets can be stored without degradation at −20° C. or lower. Finally, to use the freeze-dried platelets, users would simply inject room-temperature culture media through the filter, dissolve the frozen proteins, and the filtrate should be sterile.

Most commercial micropore filters have sterile housing designed to fit syringes with luer locks. The filters can be directly freeze-dried in their housing, capped, vacuum sealed with plastic wrap, and stored at −20° C. Injecting culture media through the filters will solubilize freeze-dried growth factors and cytokines directly into containers of culture medium. In other embodiments, the freeze-dried filters can be placed inside sterile vials. Culture solutions are injected into the vials to solubilize the filter material to create a stock solution of growth factors and cytokines, which can then be injected into the culture medium. An alternative is to remove the filters from their housing and place the filter in vials that can then be vacuum-sealed for more efficient storage.

Freezing dried platelets have many advantages over the traditional method of lysing platelets by freeze and thawing the platelets 3-4 times. Platelets become activated when they come into contact with collagen and von Willebrand factor, thrombin, or a negatively charged surface (such as glass). Platelets posses protease activated receptors (PAR) can be activated through several pathways (Yun S H, et al. (2016). Biomed. Res. Intl. 9060143). The traditional method of freeze-thawing take hours and consumes much energy. The end product is a frozen or wet slurry of partially lysed platelets that may not last in frozen storage as long as freeze-dried material. Freeze-dried material can be rapidly and easily quantified by weight.

Activation of PDP for use as Growth Media for Cell Cultures

UCB contains high concentrations of the anti-coagulant citrate-phosphate-dextrose (CPD). Both citrate and phosphates bind calcium ions, lowering calcium ionic activity in culture medium and inhibit cell growth, which requires calcium ions. When UCB PDP or PRP are added to culture media in concentrations higher than 5% (ml/deciliter), the amount of CPD will lower extracellular calcium concentration sufficiently to suppress cell growth. For this reason, calcium ions must be precipitated from PDP or PRP before it can be added to culture media to stimulate cell growth.

Figure 3:
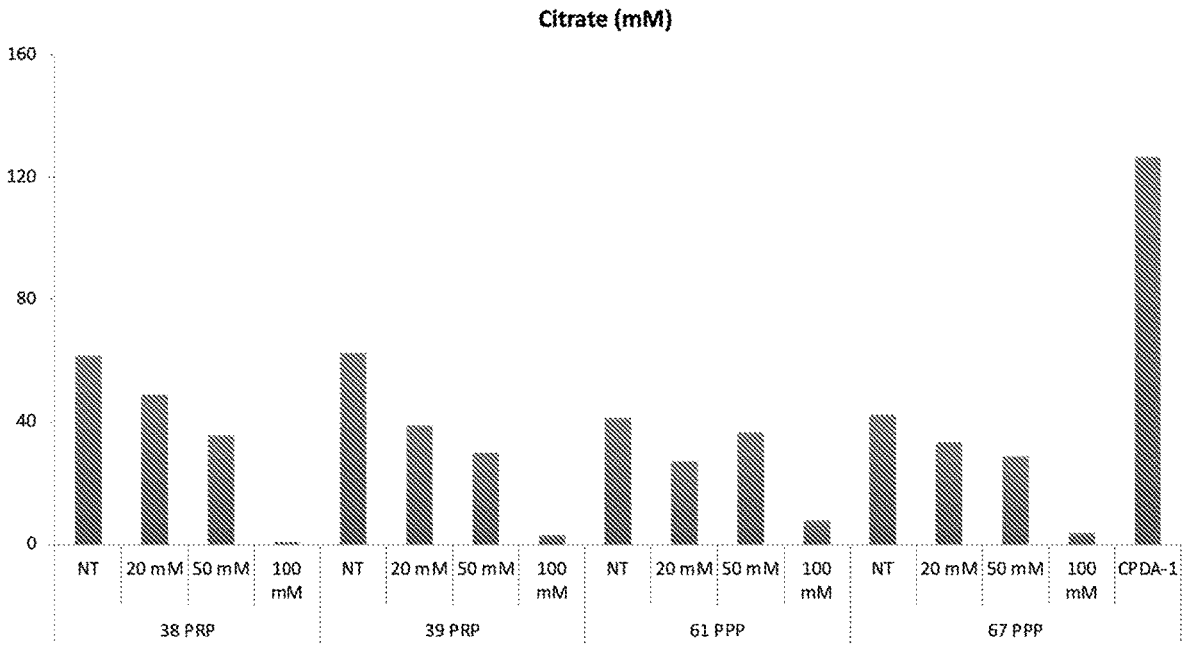
FIG. 3 shows that adding no $CaCl_2$ (NT), or enough 5 M $CaCl_2$ for the equivalent of 20 mM, 50 mM, and 100 mM Ca concentrations, precipitated CPD from PRP and PPP. Two PRP (38 PRP, 39 PRP) and two PPP (61 PPP, 67 PPP) samples were treated with the equivalent of 20, 50, and 100 mM $CaCl_2$. Increasing $CaCl_2$ to 100 mM resulted in citrate levels <5 mM for the two PRP samples and <10 mM for the 2 PPP samples. CPDA-1 is a positive control containing citrate-phosphate-dextrose.

Some investigators add calcium chloride ($CaCl_2$) to PDP or PRP in order to precipitate CPD. This is sometimes called "activation" of PDP or PRP. Adding $CaCl_2$ will precipitate not only CPD but other calcium binding proteins and platelets. A surprisingly large amount of $CaCl_2$ must be added to PDP or PRP to precipitate enough CPD to "activate" PDP or PRP to stimulate cell growth. To determine the amount of 5 M $CaCl_2$ solution to PDP or PRP, citrate concentration was measured (using ELISA with an antibody that binds citrate) in the PDP or PRP while the equivalent of 20 mM, 50 mM, and 100 mM $CaCl_2$ concentrations was added. Shown in FIG. 3, adding the amounts of 5 M $CaCl_2$ to achieve 100 mM was necessary to lower citrate concentrations close to zero.

Figure 6:
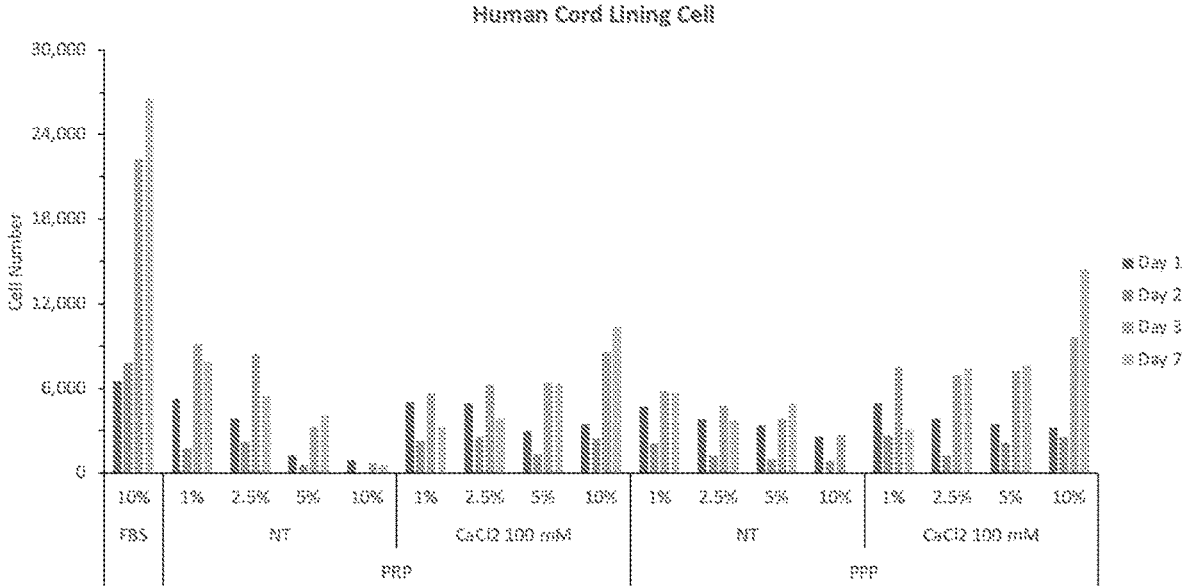
FIG. 6 is a graph showing the number of human cord lining (HCL) mesenchymal cells growing in culture medium containing PRP or PDP. PDP is platelet-depleted-plasma prepared by filtering with a micropore filter with 200 nm pores. Neither PRP nor PDP were as effective as 10% FBS in stimulating HCL mesenchymal cells cells to proliferate. Untreated PRP had delayed and smaller effects on 5% and 10% PRP concentrations compared to 10% FBS. After 100 mM $CaCl_2$ treatment, aPDP improved cell growth only in culture media with 5% and 10% aPDP. Untreated PDP was not effective in stimulating cell proliferation but $CaCl_2$-treated PDP was more effective.
Figure 7:
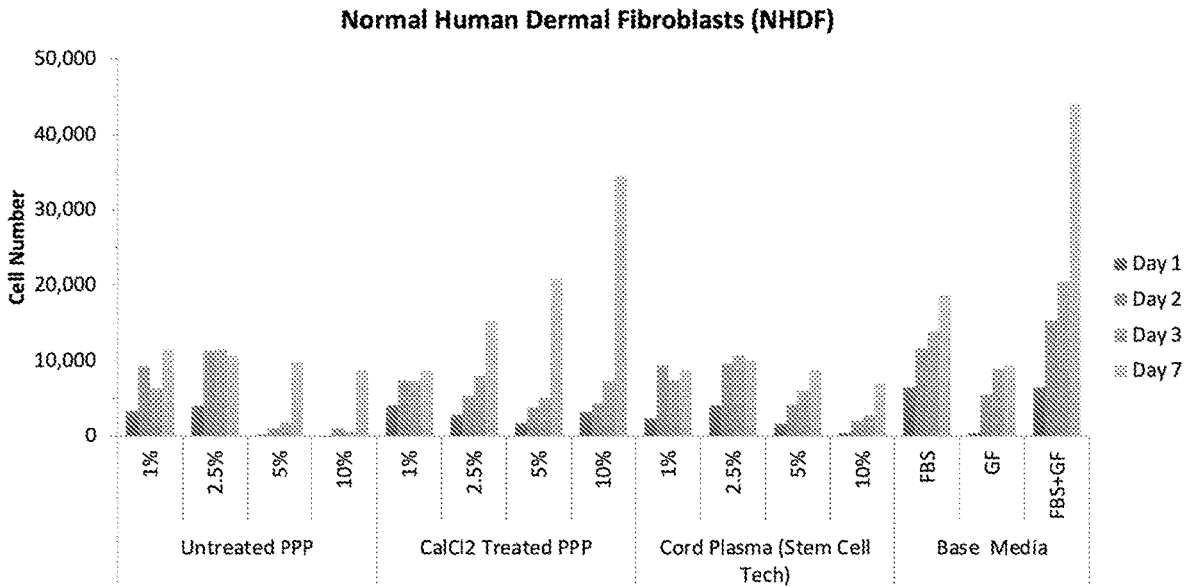
FIG. 7 is a graph showing growth of normal human dermal fibroblasts (NHDF). Untreated PPP modestly sup-ported growth but $CaCl_2$ treated PDP improved growth at 5% and 10% PPP concentrations, where cell growth sur-passed 10% FBS and also a commercial growth factor mixture (GF). "Cord plasma" was purchased from Stem Cell Tech and had limited effects on cell growth. Neither FBS nor GF alone were as good as $CaCl_2$ treated PPP. However, FBS+GF, stimulate growth to 44,000 cells at 7 days.

Adding $CaCl_2$ to the PRP precipitated many other calcium-binding proteins and molecules, as well as platelets. For this reason, the platelets should be filtered out first before adding the $CaCl_2$ and the precipitate should be removed by centrifugation or filtration before use in the cell culture medium. Activated PDP is remarkably effective in stimulating cell growth, even at 1% or lower concentrations in culture medium. FIGS. 1-5 shows the effects of different aPDP concentrations on HeLa cell cultures. Activated PDP also promotes growth of human cord lining cells (FIG. 6) and normal human dermal fibroblasts (FIG. 7).

Methods to Isolate and Cryopreserve Exosomes from Platelet-Depleted-Plasma

Platelet-depleted plasma (PDP) created by filtration or platelet-poor plasma (PPP) created by centrifugation contain exosomes and plasma proteins provide the base material from which exosomes are extracted. Traditional methods of isolating exosomes from plasma and tissues are very inefficient. The methods fall into two categories:

1. Ultracentrifugation. Exosomes are membrane-enclosed extracellular vesicles that contain mRNA, μRNA, and nuclear factors. Exosomes have proteins on their surface that bind to receptors on target cells and upload their contents into the cells. Because exosomes have low density similar to the plasma, ultra-centrifugation at 100,000×g for 24-48 hours in high osmotic solutions (sucrose gradients) is necessary to separate exosomes from plasma. The osmolarity of the solution and centrifugation forces damage exosomes, reducing the amount of undamaged exosomes that can be retrieved.

2. Partitioning of exosomes into hydrophic environments. Surface proteins bind water and increase the solubility of exosomes in aqueous environments. If water is removed from exosome surfaces, the exosomes will preferentially partition into more hydrophobic environments, such as polyethylene glycol (PEG). PEG is partly soluble in water, ethanol, acetonitrile, benzene and dichloromethane but not in more hydrophobic environments such as diethyl ether or hexane.

Commercial kits for exosomes use PEG but collect less than 20% of exosomes. In 2016, Deregibus, et al. (Deregibus, et al., 2016) used protamine, to bind negatively charged proteins and capture more exosomes (Genschmer, et al., 2019). Fujifilm[1] uses magnetic beads to capture exosomes, through phosphatidylserine receptors (Miyanishi, et al., 2007; Nakai, et al., 2016).

Most commercial kits would make 10% PEG solution (10 ml of PEG with 90 ml of phosphate buffered saline) and mixed using a vortex device. The solution looks cloudy because of the PEG bubbles. In these kits, PDP with exosomes would then be added to the 10% PEG solutions. Usually, after an hour or two at room temperature, 10-20% of the exosomes would partition into the PEG. The mixture will be centrifuged at 2500×g and, due to the higher molecular weight of PEG, the denser PEG with the exosomes would form a pellet at the bottom of the tube. The supernatant would be removed and PBS or PDP would be added to the pellet to obtain exosome-rich plasma (ERP).

The novel methods described herein differ in several ways. For example, the use of ultrasound to fragment the PEG into microbubbles that have much greater surface-to-volume ratios, which would greatly increase the interaction between exosomes and the bubbles. For example, mixing 50 ml PEG (10,000 molecular weight) into 50 ml of PBS yields 50% PEG solution. This solutions is cloudy in light because the PEG is in the form of bubbles that >340 nm in diameter. Ultrasonication of the mixture rapidly clarifies the solution, because ultrasonicated microbubbles are less than 340 nm in diameter and therefore not visible.

Another example is cooling the solution to 4° C. and keeping the solution in the refrigerator overnight. As the temperature approaches 0° C., water tends to leaves the surfaces of exosomes to participate in ice formation, reducing solubility of exosomes in the aqueous phase and increasing exosome movement into the PEG microbubbles. After 8 hours at 4° C., >90% of the exosomes have partitioned into the PEG.

Another example is centrifuging the PEG mixture at 2500×g for 30 minutes, removal of the supernatant, and then freezing the exosomes in the PEG to −170° C. PEG solutions are used in anti-freeze solutions for cars, preventing ice formation that could damage exosomes. When the frozen pellets of exosomes (exosome pellets) are thawed at room temperature, PBS or PDP would be added to create exosome-rich plasma of the appropriate exosome concentration. Methods to Isolate Globulins, Albumin/Fibrinogen from Exosome-Depleted Plasma Exosome depleted plasma (EDP) contains pre-dominantly albumin, globulins, and fibrinogen in order of prevalence.

i. Albumen is the most prevalent protein in umbilical cord blood and peripheral blood, accounting for over 50% of plasma protein. Growth factors, hormones, and cytokines are bound by the albumin.

ii. Globulins include immunoglobulins such as IgA, IgG, and IgM, which is frequently used to treat autoimmune diseases. Many globulins are signalling molecules. Some globulins are cold-sensitive cryoglobulins that bind and cross link the other globulins.

iii. The clotting protein fibrinogen is widely available from peripheral blood and should not be very different from adult fibrinogen but it can be readily removed by inducing clot formation, centrifuging the clot out. This can be done by adding thrombin and calcium.

Because the second step of isolating exosomes is cooling PDP to 4° C. overnight and centrifuging the mixture to form a PEG pellet, most of the globulins would have been cooled to the point of forming a gel. The globulin gel can be poured into a vial, followed by pipetting the albumin-fibrinogen solution into a vial, and freeze-drying both the gel and the albumin-fibrinogen. The PEG pellet containing the exosomes (exosomes pellet) can then be placed in a vial and frozen.

If users want to have the albumin without the fibrinogen, this can be taken care of by adding thrombin solution and inducing a centrifuging, centrifuging the clot down, and using the supernatant that should contain mostly albumin. PDP can of course be used directly as a growth medium that would be added directly to culture media like FBS. Exosomes, albumin, and freeze dried platelets could also be added to the culture media individually or together.

In other embodiments, all the above components of plasma globulins and albumin-fibrinogen can be used for research and for clinical therapy.
Methods of Using UCB Plasma Components for Culturing Mammalian Cells An embodiment of a method of culturing mammalian cells includes growing a population of mammalian cells in a cell culture medium that includes a growth solution made according to the methods described above. The growth solution can include PRP, PDP, freeze-dried platelets, exosomes, and/or albumin and/or growth factors. In the method, the mammalian cells are typically human cells, and the tissue source is typically UCB. Any type of mammalian cell can be cultured using the methods and growth solution described herein, including, as non-limiting examples, Hela cells, mesenchymal stem cells, normal dermal cells, hepatocytes, and fertilized ova.

The term "culturing" refers to maintaining cells under conditions in which they can proliferate. For example, cells are cultured in media with one of the UCB components with additional growth factors or cytokines, i.e. a growth factor or cytokine cocktail. Methods of culturing and growing mammalian cells are well known in the art.

According to the methods, cell culture medium, and growth solutions described herein, $CaCl_2$-treated UCB PDP can be used as a culture media for growing human cells for transplantation. UCB PDP treated with the equivalent of 100 mM of $CaCl_2$ is an effective and safe growth adjuvant for human cell cultures. UCB is more sterile than adult human serum which may be infected with many diseases. This is in part due to the maternal-placental barrier that excludes many maternal infections from the fetus during pregnancy. UCB units collected are tested for many common diseases and the mother's blood is also tested for antibodies against common diseases. UCB PDP is likely to be the safest source of human plasma for growing cells for transplantation.

In some embodiments, some human primary cells may require additives to the growth media described herein. In such embodiments, a UCB PDP growth solution as described herein serves as an excellent base upon which additional factors can be added. This approach provides an economic and efficient xeno-free growth media for growing human cells for transplantation. For cells that do not grow as well in activated PDP, addition of platelets may be helpful. For certain cells, such as UCB and bone marrow cells, certain growth factors, cytokines, and other factors (such as lithium—see U.S. Pat. No. 8,852,938 incorporated by reference herein) may be useful.

UCB has several major advantages over FBS obtained from cows, for example, as a source of growth factors for cell culture. First, FBS is getting progressively more expensive due to "mad cow's disease" or bovine spongiform encephalopathy (BSE) affecting cows in the Americas, Europe, and Africa. The only sources of FBS that are currently certified BSE-free are in Australia and New Zealand. If BSE appears in either of these two countries, the world supply of FBS may not be severely curtailed. UCB PDP, however, will be available because >30 million babies are born each year. The average size of a cord blood unit is 80 ml and the plasma volume is about 40 ml or about 1.2 billion liters of UCB plasma, more than sufficient to meet cell culture needs. In India, the use of FBS for cell culture is abhorrent to the predominantly Hindu population that views cows as sacred, because it requires harvesting 7 million calves from pregnant cows for their serum. In India, 90,000 thousand babies are born every day, more than enough to supply all the growth factor needs of the cell culture industry. Only about 5% of the cord blood is currently being collected in India. If even 20% of all cord blood is collected in India or 3.6 million ml of plasma per day, this would be more than sufficient to meet the current need for FBS for all cell culture in the world. Since 1-5% of UCB PDP will replace 10% FBS using the methods described herein, it is estimated that UCB PDP could replace FBS at $20/ml; FBS currently costs about $5/ml.

Compositions and Methods of Treatment

The platelets, exosomes, globulins, fibrinogen, and albumin isolated by the above-described methods have beneficial effects on many conditions and can be applied in many ways. For example, exosomes promote repair of tissue damage including neurodegenerative and autoimmune. UCB globulins may serve as a substitute of intravenous immunoglobulin therapy. Fibrinogen and clotting factor are used to treat patients with clotting deficiencies, and can be used as a surgical glue. Albumin is a useful excipient for transporting cells.

This disclosure also provides pharmaceutical compositions including freeze-dried platelets, exosomes, fibrinogen, and albumin isolated by the methods as described above. A pharmaceutical composition may include an appropriate vehicle for delivery of platelets, exosomes, fibrinogen, and/ or albumin to a subject in need thereof. In some embodiments, the compositions may also include a cryopreservant and/or pharmaceutically acceptable carrier.

Accordingly, this disclosure provides a method for regenerating tissue in a subject. The method includes administering to the subject an effective amount of the exosomes isolated by the methods described herein. In the method, the subject is typically a human suffering from at least one of the following disorders: tissue damage, brain degeneration, central nervous system injury and degeneration, and cardiovascular degeneration.

This disclosure also provides a method for treating fibrinogenemia or a clotting deficiency in a subject. The method includes administering to the subject suffering from fibrinogenemia or a clotting deficiency an effective amount of the fibrinogen isolated by the methods described herein.

This disclosure further provides a method for treating dry-eye syndrome, an orthopedic disorder, or a dental disorder in a subject. The method includes administering to a subject suffering from dry-eye syndrome, an orthopedic disorder, or a dental disorder, an effective amount of the platelets isolated by the methods described herein.

The dose and the administration frequency will depend on the clinical signs, which confirm maintenance of the remission phase, with the reduction or absence of at least one or more preferably more than one clinical sign of the acute phase known to the person skilled in the art. More generally, dose and frequency will depend in part on the recession of pathological signs and clinical and subclinical symptoms of a disease condition or disorder contemplated for treatment with the above-described composition. Dosages and administration regimen can be adjusted depending on the age, sex, physical condition of administered as well as the benefit of the conjugate and side effects in the patient or mammalian subject to be treated and the judgment of the physician, as is appreciated by those skilled in the art.

As used herein, the term "subject" refers to a vertebrate, and in some exemplary aspects, a mammal. Such mammals include, but are not limited to, mammals of the order Rodentia, such as mice and rats, and mammals of the order Lagomorpha, such as rabbits, mammals from the order Carnivora, including Felines (cats) and canines (dogs), mammals from the order Artiodactyla, including bovines (cows) and swines (pigs) or of the order Perissodactyla, including Equines (horses), mammals from the order Primates, Ceboids, or Simoids (monkeys) and of the order Anthropoids (humans and apes). In exemplary aspects, the mammal is a mouse. In more exemplary aspects, the mammal is a human.

As used herein, the term "administering" refers to delivery of exosomes, fibrinogen or platelets, by many routes including, without limitation, oral, intranasal, intraocular, intravenous, intraosseous, intraperitoneal, intraspinal, intramuscular, intra-articular, intraventricular, intracranial, intralesional, intratracheal, intrathecal, subcutaneous, intradermal, transdermal, or transmucosal administration.

As used herein, the term "effective amount" or "therapeutically effective amount" refers to an amount which results in measurable amelioration of at least one symptom or parameter of a specific disorder. A therapeutically effective amount of the above-described plasma exosomes, platelets, extracellular vesicles, fibrinogen, and clotting factors can be determined by methods known in the art. An effective amount for treating a disorder can be determined by empirical methods known to those of ordinary skill in the art. The exact amount to be administered to a patient will vary depending on the state and severity of the disorder and the physical condition of the patient. A measurable amelioration of any symptom or parameter can be determined by a person skilled in the art or reported by the patient to the physician. It will be understood that any clinically or statistically significant attenuation or amelioration of any symptom or parameter of the above-described disorders is within the scope of the invention. Clinically significant attenuation or amelioration means perceptible to the patient and/or to the physician.

Pharmaceutical compositions can be prepared by mixing a therapeutically effective amount of exosomes, fibrinogen or platelets and, optionally, other active agents/compounds, with a pharmaceutically acceptable carrier. The carrier refers to a diluent, excipient, or vehicle with which a therapeutic is administered. The carrier can have different forms, depending on the route of administration. The carriers can be sterile liquids, such as water and oils. Water or aqueous solution, saline solutions, and aqueous dextrose and glycerol solutions are preferably employed as carriers, particularly for injectable solutions. Suitable pharmaceutical carriers are described in "Remington's Pharmaceutical Sciences" by E. W. Martin, 18th Edition. For example, the compositions can be prepared by mixing with conventional pharmaceutical excipients and methods of preparation. Excipients may be mixed with disintegrating agents, solvents, granulating agents, moisturizers, and binders.

The phrase "pharmaceutically acceptable" refers to molecular entities and other ingredients of such compositions that are physiologically tolerable and do not typically produce unwanted reactions when administered to a human. Preferably, the term "pharmaceutically acceptable" means approved by a regulatory agency of the federal or a state government or listed in the U.S. Pharmacopeia or other generally recognized pharmacopeias for use in mammals, and more particularly in humans. Pharmaceutically acceptable salts, esters, amides, and prodrugs refers to those salts (e.g., carboxylate salts, amino acid addition salts), esters, amides, and prodrugs which are, within the scope of sound medical judgment, suitable for use in contact with the tissues of patients without undue toxicity, irritation, allergic response, and the like, commensurate with a reasonable benefit/risk ratio, and effective for their intended use.

The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

All methods described herein are performed in any suitable order unless otherwise indicated herein or otherwise clearly contradicted by context. In regard to any of the methods provided, the steps of the method may occur simultaneously or sequentially. When the steps of the method occur sequentially, the steps may occur in any order, unless noted otherwise.

In cases in which a method comprises a combination of steps, each and every combination or sub-combination of the steps is encompassed within the scope of the disclosure, unless otherwise noted herein.

Each publication, patent application, patent, and other reference cited herein is incorporated by reference in its entirety to the extent that it is not inconsistent with the present disclosure. Publications disclosed herein are provided solely for their disclosure prior to the filing date of the present invention. Nothing herein is to be construed as an admission that the present invention is not entitled to antedate such publication by virtue of prior invention. Further, the dates of publication provided may be different from the actual publication dates which may need to be independently confirmed.

It is understood that the examples and embodiments described herein are for illustrative purposes only and that various modifications or changes in light thereof will be suggested to persons skilled in the art and are to be included within the spirit and purview of this application and scope of the appended claims.

Use of UCB Platelet-Depleted Plasma and Exosomes

UCB plasma and exosomes differ from those of adult blood in several important ways. UCB is made by the placenta and is the primary means of communication between the placenta, uterus, and fetus, passing message via hormone, cytokines, chemokines, and exosomes in the plasma. So, UCB plasma contains factors that adult blood does not have. UCB also has more and different stem and progenitor cells than adult blood, including higher proportion of monocytes. Monocytes are progenitors for macrophages as well as dendritic cells. These cells secrete factors and exosomes that differ from adult blood. UCB platelets and plasma are used as a substitute for FBS as growth media for human mesenchymal stem cell (MSC) cultures. It has been known that UCB plasma contains very high concentrations of transforming growth factor beta-1 (TGF-b1), vascular endothelial growth factor (VEGF), platelet-derived growth factor (PDGF-AAA, PDGF-BBB), and endothelial growth factor (EGF), as well as chemokines (RANTES, GRO, MCP-1, Eotaxin, Fractakline) and immune factors (IL-12p70, IFNy, IL-4, IL-17A, IL-10, and IL13). Many of these factors are used in defined media for growing human MSC cells. The main problem with using UCB plasma as growth media is the presence of CPD in cord blood. CPD is an anti-coagulant that binds and lowers calcium ionic activity sufficiently to stop clotting of blood. Lowering calcium ionic activity will also stop cell growth. This is why UCB plasma promotes growth only when enough $CaCl_2$ is applied to restore calcium to levels required for cell growth. In the experiments described below, adding 20 mM $CaCl_2$ is not sufficient to bind and precipitate the CPD in culture, and that adding the equivalent of 100 mM $CaCl_2$ restored calcium ionic activity enough to allow cells to grow. These results show that 1% "activated" PDP stimulates HeLa cells to grow as much as 10% FBS.

The growth factors, chemokines, and immune factors known to be present in plasma were shown in the experiments described below to stimulate cell growth once calcium ionic activity is restored. The experiments also showed that exosomes in PDP contribute to the growth because adding $1.2 \times 10^{11}$ particles per ml into the culture medium at 10% concentration also stimulated the cells to grow, although not as much as 10% PDP. Treating PDP with the equivalent of 100 mM of $CaCl_2$ eliminates cell growth inhibitory effects of CDP and shows that PDP strongly stimulates HeLa cell growth. HeLa cells need growth factors to grow because they will not grow with just culture medium. Most laboratories now use FBS as the source of growth media to grow cells. Many studies have shown that cells grown in FBS express bovine proteins and will be immune rejected. The US Food and Drug Administration (FDA) has advised that cells intended to human use must not be grown or stored in media that contains animal proteins and particularly FBS, because more than half of people have antibodies against FBS due to drinking milk. The only source of human growth factors is lysed platelets from adult blood. The novel methods described herein include UCB PDP as a better and safer source.

One example of a condition that UCB exosomes may play a major beneficial role in treating is hypoxic-ischemic encephalopathy (HIE), a condition that affects about 0.4% of babies, due to umbilical cord blood wrapping around the neck, slow and prolonged passage through the birth canal, or severe anemia that may fail to carry oxygen to the baby. Exosomes can pass through the blood brain barrier (BBB) and can be given intravenously (Perets et al. Nano Lett. 2019; 19(6):3422-31; Osorio-Querejeta et al., Front Mol Neurosci. 2018; 11:434). Several clinical trials (Tsuji et al. Sci Rep. 2020; 10(1):4603) and animal studies have shown that UCB transfusion in neonates with HIE improves neurological recovery from HIE. Another example of a condition that UCB exosomes may be beneficial in treating is stroke. A third example of a condition that UCB exosomes may be beneficial in treating is hypo-endometria, thin uterine endometrial lining, which is the primary reason that fertilized eggs do not implant in women with thin endometrial lining of <0.5 cm. Since UCB exosomes carry many signals that stimulate vascularization and blood flow, placement of UCB exosomes into the intrauterine cavity may stimulate endometrial growth. This could be done at the time that eggs are retrieved from the ovaries. Concentrated exosome rich plasma (ERP) can be injected into the uterine cavity a week before implantation. Endometrium lining can be readily monitored by ultrasound. A fourth example of a condition that can be treated with UCB exosomes are autoimmune conditions. UCB exosomes contain many factors that suppress the immune system, thus injection of UCB exosomes isolated according to the methods described herein may inhibit autoimmune conditions, such as multiple sclerosis, systemic lupus erythematosus, rheumatic arthritis, psoriatic arthritis, and others. Intravenous injection of UCB exosomes may relieve acute autoimmune attacks.

EXAMPLES

Example 1 i. Isolation of Platelets, EVs, Exosomes, Albumin, Fibrinogen, Globulin and Clotting Factors Examples of novel methods of isolation of platelets, EVs, and exosomes from UCB PRP include:

(a) A method to isolate platelets and EVs and form freeze-dried platelets. PRP is filtered with a 0.22μ filter to capture platelets and extracellular vesicles, which are freeze-dried as a source of growth factors.

(b) A method to isolate exosomes and precipitate the anti-coagulant CPD. To isolate exosomes, platelet-depleted plasma (PDP) is added to a 10% PEG and 100 mM CaCl$_2$ solution. The exosomes partition into PEG while the CaCl$_2$ precipitates the anticoagulant CPD. The solution is cooled to 4° C. and centrifuged at 3000 g for 20 minutes.

(c) A method to isolate albumen, fibrinogen, globulin, and clotting factors. The cooling of the PPP to 4° C. activates temperature-sensitive globulins in the plasma to bind and crosslink fibrinogen and fibrin. The cryoprecipitate of fibrinogen and globulins, as well as other clotting factors, is gel-like. The supernatant, containing the albumin and other plasma protein, is poured out into a separate container for freeze drying. The cryoprecipitate is aspirated into a second container for freeze-drying. The exosome/PEG pellet is frozen at −20° C. and the PEG protects the exosomes from freeze damage.

Example 2 ii. UCB Freeze-Dried Platelets

In a novel method of separating UCB PRP, UCB is first separated into PRP, MNC, and RCF using, for example, the Syngen (Thermogenesis) device to centrifuge the UCB in stages to maximize platelet concentration in the plasma. The PRP layer is withdrawn with a 60 ml syringe, and filtered with a 0.22μ Millipore filter to remove particles >220 nm in diameter. The Millipore filter containing EVs and platelets are placed into a sterile container and freeze-dried to release growth factors. The container can be stored at −20° C.

In this method, the filtering and freeze-drying the platelets is novel. In contrast, most laboratories and industries centrifuge PRP to collect platelets, pipette out the supernatant, and then repeatedly freeze-thaw the pellet to release the growth factors. Filtering collects both platelets and EVs that contain growth factors. In the methods described herein, freeze-drying releases and concentrates growth factors better than multiple freeze-thaws. This process requires less manipulation of the sample and can be done in a completely closed system. To thaw and dissolve the freeze-dried growth factors, culture media is injected into the container to dissolve growth factors on the filter and the resulting growth solution can be withdrawn from the container and placed into the cell culture dish.

Example 3

UCB Plasma Exosomes, Fibrinogen, and Albumin

In a novel method of isolating plasma exosomes, fibrinogen and albumin from UCB PRP, PDP is added into a centrifuge tube containing a solution of 10% polyethylene glycol (PEG, 10,000 MW) and 100 mM CaCl$_2$ and cooled to 4° C. The exosomes partition into the PEG while the CaCl$_2$ precipitates CPD and cooling activates cold-sensitive globulins in the plasma that bind fibrinogen to form a cryoprecipitate. After centrifugation at 3000 g for 20 minutes, exosomes form a PEG pellet at the bottom of the tube, the cold-induced globulin gel, and the supernatant contains albumin and other plasma proteins. After pouring the supernatant out, the gel-like cryoprecipitate is aspirated and freeze-dried for fibrinogen and clotting factors. The exosome pellet can be frozen at −20° C. with the PEG serving as a cryopreservant.

This novel method uses a combination of PEG and CaCl$_2$ to isolate exosomes and to precipitate CPD in one short (20-minute) and low-speed centrifugation step. The following advantages are provided by the novel method:

i. This procedure precipitates CPD and isolates exosomes in one step. Due to the low speed centrifugation, large volumes can be processed at a time, i.e. 60 ml of plasma from a unit. This is much more efficient than repeatedly spinning small volumes of plasma at 120,000 g for 18 hours.

ii. The PEG will prevent crystallization of the exosomes and cryopreserve the exosomes.

iii. The procedure isolates fibrinogen and albumen for freeze-drying.

Example 4

Exosome Isolation from UCB and PDP

Centrifuging UCB separates the three main components of UCB: PRP, mononuclear cells (MNC), and RCF. The PRP will be separated from the UCB and filtered with a 0.22 μm micropore filter to remove platelets, yielding PDP. The filter will remove platelets and extracellular vesicles >220 nm in diameters. The exosomes should remain. In an embodiment of a method of producing PDP, UCB is thawed, the UCB is centrifuged resulting in a PRP fraction, the PRP fraction is separated, and platelets are removed by centrifuging PPP or filtering PDP and cellular debris and extracellular vesicles larger than 220 nm, resulting in a PDP portion that includes CDP, exosomes, and plasma proteins.

Depending on the platelet concentration in the PRP, filtering can be done with the 0.22 μm filter, centrifuging PRP to obtain a pellet of platelets, and filtering with a 1.0μ filter to remove platelets before filtering with the 0.22 μm filter to remove >220 nm diameter extracellular vesicles. The platelets pelleted from centrifugation or the filtered platelet will be freeze-dried (lyophilized) so that all the growth factors in the platelets will be frozen and available to be dissolved into culture media.

Cord blood is anti-coagulated with CPD that reduces extracellular calcium activity in cell culture media. CPD prevents clotting by binding calcium ions and reducing extracellular calcium ionic activity below the level required for clotting. The reduction of calcium ionic activity is sufficient to prevent growth of cells in culture. To reduce CPD to a level that it does not prevent cell growth, 20 mM CaCl$_2$ was added to PRP. The CaCl$_2$ should bind the CPD. The results are shown in FIG. 1.

Adding 20 mM CaCl$_2$ to PRP had complicated effects on HeLa cell growth. On the left of the graph in FIG. 1, 10% FBS and 10% human serum (HS) caused rapid cell growth at day 1, 2, 4, and 7 days after plating. When UCB PRP was added, effects of 5% PRP concentration were delayed but reached the same level at 7 days. However, 10-20% concentrations of PRP suppressed growth of the cells. This is interpreted to mean that 5% PRP stimulates growth of HeLa cells in culture like 10% FBS or 10% HS but higher 10-20% concentration of PRP inhibited growth because they add sufficient CPD to lower extracellular calcium to prevent cell growth.

Adding 20 mM $CaCl_2$ to the PRP restored cell growth at 10 mM and 20 mM PRP. But, when the $CaCl_2$-treated PRP was centrifuged down (spun down), the inhibition of growth returned at 10% and 20% PRP concentration. This may have been due to the CPD that bound calcium ions and lowered extracellular calcium activity, thereby inhibiting cell growth. Adding 20 mM $CaCl_2$ prevented this inhibition but it was clearly not enough because centrifugation of the $CaCl_2$-treated PRP and removing the precipitate restored the growth inhibition of 10-20% PRP (far right section of FIG. 1).

Figure 2:
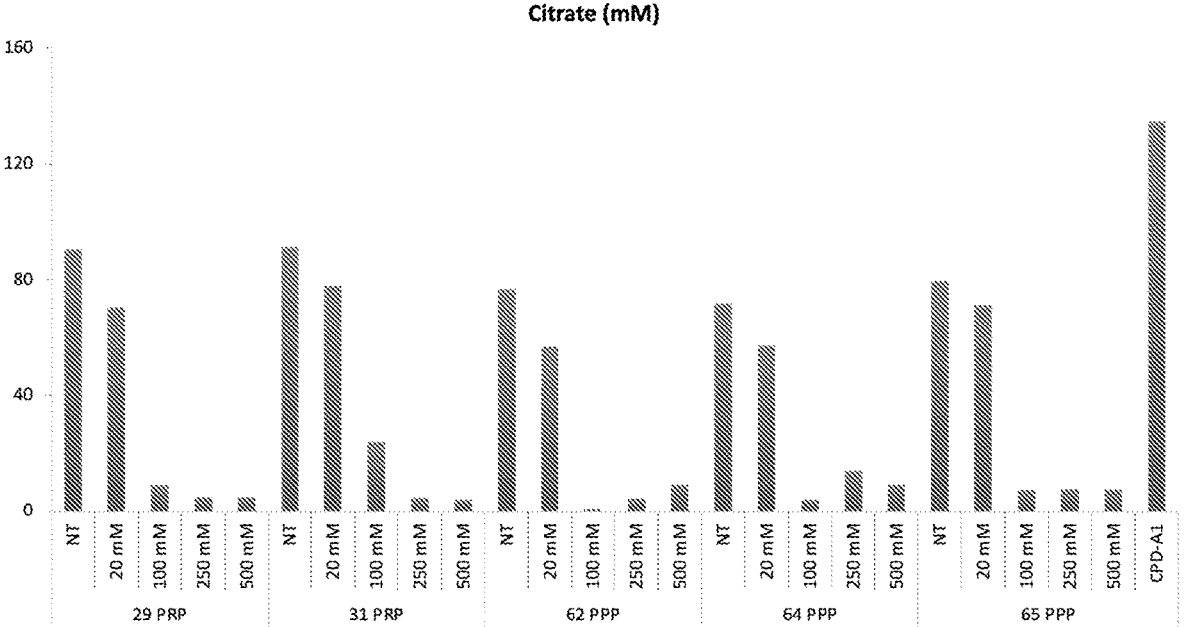
FIG. 2 is a graph showing citrate concentrations in PRP and platelet-poor-plasma (PPP) after adding increasing amounts of 5M $CaCl_2$ were added to PRP and PPP, ranging from NT (no treatment) to 20 mM, 100 mM, 250 mM, and 500 mM calcium concentrations, To assess the effects of adding 20-100 mM $CaCl_2$ on citrate concentrations of plasma, citrate levels (mM) were measured by ELISA. The leftmost part of the graph (29 PRP) showed that NT had about 90 mM citrate. Adding 20 mM $CaCl_2$ lowered citrate to 70 mM and adding 100 mM $CaCl_2$ lowered citrate to <10 mM. In another sample (31 PRP), adding 100 mM $CaCl_2$ reduced citrate to 20 mM. In a third sample of PPP (62 PPP), adding 100 mM $CaCl_2$ resulted in no citrate. In a fourth sample of PPP (64 PPP), adding 100 mM $CaCl_2$ resulted in <5 mM citrate. In a fifth sample of PPP (65 PPP), adding 100 mM $CaCl_2$ resulted in <10 mM citrate. CPD-A1 is the citrate-phosphate-dextrose (CPD) solution that is placed in the collection bag.

Effects of Untreated and $CaCl_2$-Treated PDP and PRP on Cell Growth in Culture:

The complicated effects of adding 20 mM $CaCl_2$ to PRP and finding that spinning down the precipitate restored the growth inhibition of 10-20% the $CaCl_2$-treated PRP (far right section of FIG. 1) suggested that 20 mM did not eliminate all CPD. To determine whether the CPD had been eliminated, calcium-specific ion-selective electrodes could not be used to measure extracellular calcium because CPD interfered with the calcium ionic activity measurements. Instead, the enzyme-linked immunosorbent assay (ELISA) was used to measure citrate concentration. Increasing amounts of $CaCl_2$ were added to increase the concentration of $CaCl_2$ to 20, 100, 250, and 500 mM, this would indicate which amount of added $CaCl_2$ reduced citrate levels close to zero. FIG. 2 shows these results.

$CaCl_2$ Activation of PRP and PDP:

The results of the experiment shown in FIG. 2 suggest that adding $CaCl_2$ to raise Ca concentration to the equivalent of 100 mM in the plasma reduced citrate to low levels in PRP and to near zero levels in PPP. PPP refers to platelet that has been centrifuged to pellet platelets and remove the supernatant; there may be some platelets remaining. PDP refers to filtered plasma which eliminates all platelets. Although some citrate may still be present in the plasma after the equivalent of 100 mM is added, the amount of citrate is not enough to lower Ca ionic concentrations low enough to prevent cell growth. To minimize the volume added to the solution, the highest concentration of $CaCl_2$ (5M) was used to add calcium to the plasma.

Note that adding of $CaCl_2$ to precipitate CPD in PRP or PPP is only necessary if PDP is being used to provide growth media for cell culture. If PDP were being injected intravenously into a person, the amount of calcium in the body fluids is more than enough to neutralize the CPD. Note that even when the equivalent of $CaCl_2$ to 500 mM was added, it did not eliminate all the citrate, which suggested that the assay does not measure zero citrate accurately. To confirm, the experiment was repeated to measure citrate after adding enough $CaCl_2$ to reach 20, 50, and 100 mM, shown in FIG. 3.

The data suggest that adding the equivalent of 100 mM of $CaCl_2$ is sufficient to reduce citrate levels to low levels in PRP samples (38 PRP and 39 PRP). However, in PPP samples (61 PPP and 67 PPP) adding enough $CaCl_2$ to reach 100 mM concentration reduced citrate to <10 mM. In plasma that received no treatment (NT), citrate concentrations appear to be close to 60 mM in PRP but closer to 40 mM in PPP, suggesting that there may be some background citrate activity in PRP.

The molecular weight of $CaCl_2$ is 110.98 grams, 100 mM is 11.098 grams of $CaCl_2$ per liter, and 5M $CaCl_2$ is 554.9 grams/liter. For example, if one had 100 ml of plasma, one would add 1.1098 grams or about 2.0 ml of 5 M $CaCl_2$ to 98 ml of plasma. Most cord blood bags have CPD but some have CPD plus 0.25 mM adenine (CPDA), which prolongs red blood cell life.

A typical 300 ml cord blood collection unit has 27 ml of CPD solution (Gibson et al. Bibl Haematol. 1968; 29:758-63), containing 0.92 g Sodium Citrate (dihydrate) USP; 0.89 g Dextrose (monohydrate) USP; 114.5 mg citric acid (monohydrate) USP; 87.9 mg Mono basic sodium phosphate (dihydrate), USP. The molecular weight of trisodium citrate dihydrate is 294.1 g/mole, of mono basic sodium phosphate (dihydrate) is 156.01 g/mole, and of dextrose monohydrate is 198.17 g/mole.

Figure 4:
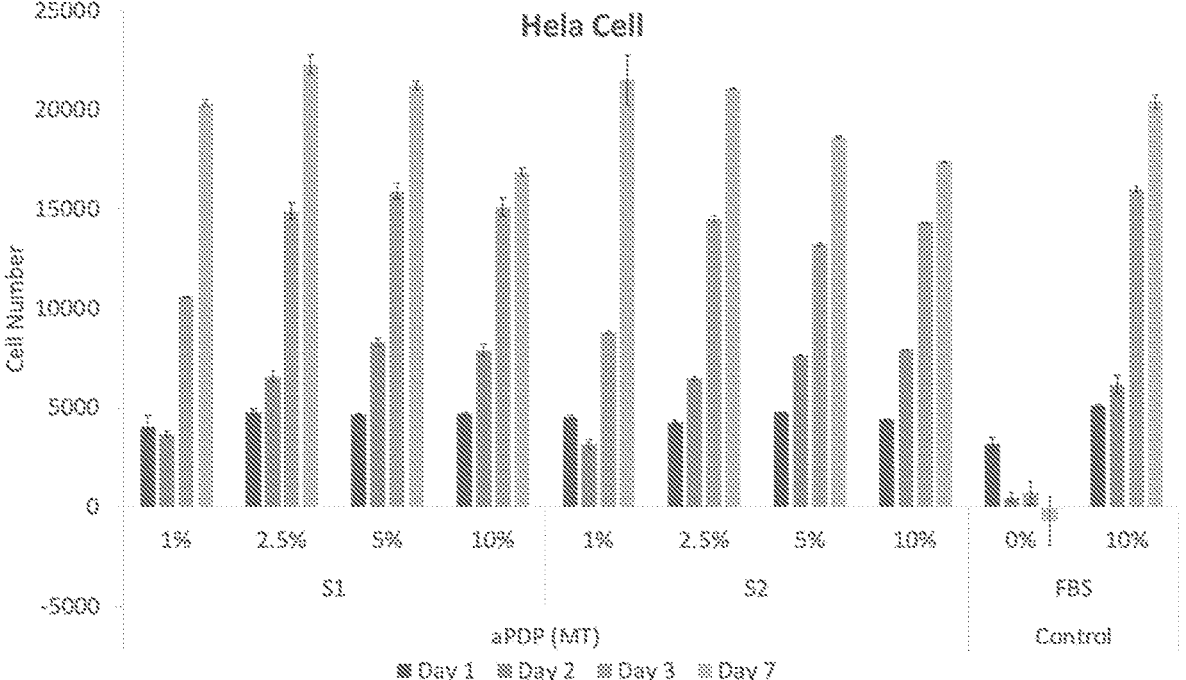
FIG. 4 is a graph showing HeLa cell growth in culture containing 1% to 10% activated platelet-depleted-plasma (aPDP) by adding 5 M $CaCl_2$ to the equivalent of 100 mM. S1 refers to PDP that was collected in October 2017 and then stored frozen at –20° C. until August 2020. S2 refers to PDP collected in November of 2019 and then stored frozen at –20° C. until August 2020. The PDP was thawed and activated by adding 5 M $CaCl_2$ solution equivalent to 100 mM concentration. FBS is the positive control and 0% FBS is the negative control. Cell proliferation is represented by cell count at 1, 2, 3, and 7 days after starting the initial culture of 3000 cells in 1%, 2.5%, 5%, and 10% aPDP.

Effects of $CaCl_2$-Treated PDP on Hela Cell Growth:

HeLa cells are derived from a human cervical carcinoma cell line. These cells require FBS to grow. The rightmost graph in FIG. 4 shows showed 3000 cells on the first day and then little or no cells at 2, 3, and 7 days. With 10% FBS, the cells have grown to >4000 cells by the first day, 5000 cells by the second day, 15,000 cells by the $3^{rd}$ day, and 18,000 cells by the $7^{th}$ day.

A 1% concentration of 51 aPDP collected in October 2017 and stored for 3 years at −20° C. until August 2017, had a slower start in stimulating cell proliferation but caught up by Day 7. At 2.5% and 5% concentrations, 2.5% and 5% aPDP was better than 10% FBS at 7 days. At 10%, aPDP was not as effective as 10% FBS at 7 days.

At 1-5% concentrations, S2 aPDP collected in November 2017 and stored for about 10 months, also stimulated HeLA proliferation, again with the delay in response that reached the 7-day result that was similar to 10% FBS. The data indicates two surprising findings: 1% aPDP effectively stimulates HeLa cell growth and is as potent as 10% FBS whether the cells were stored frozen at −20° C. for 3 years or for 3 years in 2020.

TABLE 1

Added calcium, pH, and total protein (mg/ml) in four plasma samples. PRP is platelet-rich-plasma, PPP is platelet-poor-plasma, prepared by centrifugation. Note that $CaCl_2$ addition reduced the pH of the cord blood. In all the samples, adding $CaCl_2$ increased the weight of total protein in mg/ml.

| Sample # | $CaCl_2$ (mM) | pH | Total Protein (mg/mL) |
|---|---|---|---|
| 38 PRP | 0 | 7.6 | 33.8 |
| | 100 | 6.3 | 47.5 |
| 39 PRP | 0 | 7.5 | 32.2 |
| | 100 | 6.4 | 36.1 |
| 61 PPP | 0 | 7.6 | 44.7 |
| | 100 | 6.4 | 46.0 |
| 67 PPP | 0 | 7.5 | 53.8 |
| | 100 | 6.3 | 42.3 |
| FBS | | | 40.9 |

Table 1 shows plasma pH and total protein weight in PRP and PPP samples that before and after treatment with $CaCl_2$. Before treatment, the pH was normal at 7.4-7.6. After $CaCl_2$ treatment, the pH drops to 6.4, perhaps contributing to reduced growth in the cultures. See FIG. 5, an experiment showing that in the presence of platelets, i.e. PRP at 1%, 2.5%, and 5.0% concentrations increases cell counts and only 10% PRP seems to be inhibited. When 100 mM $CaCl_2$ was added, it improved the growth rates. In the absence of platelets, i.e. 10% PPP appeared not to do very well without $CaCl_2$ activation.

Effect of $CaCl_2$ Treatment of PRP and PPP on Human Cord Lining Cells

HCL cells are mesenchymal cells (CD105+) with as many as 10% mesenchymal stem cells. Low concentrations (1% and 2.5%) of untreated PDP will support HCL growth. Higher concentrations (5% and 10%) of untreated PDP were ineffective (see FIG. 6). Activation with 100 mM $CaCl_2$ did improve cell growth, particularly at the higher 5% and 10% concentrations of PRP.

These results suggest that PDP should have the best effect on mesenchymal stem cell growth at 10% concentration and with 100 ml $CaCl_2$ activation. The growth effect is not quite as good as 10% FBS. About 6% of the cord lining cells are Muse cells, which are not known for their high rate of cell growth. On the other hand, 10% concentrations of $CaCl_2$-activated PPP only resulted in half the number of cells at 7 days compared to 10% FBS.

$CaCl_2$ activation improves cell growth, especially at higher doses of PPP. Untreated PRP is better than untreated PPP at 1% and 2.5% but not at 5% or 10% concentration. The best human growth media for mesenchymal cells is 10% PPP activated with $CaCl_2$.

Effect of $CaCl_2$ Treatment of PRP and PPP on Normal Human Dermal Fibroblasts:

Fibroblasts apparently need both 10% FBS and growth factors to grow optimally. 10% FBS by itself did stimulate growth with a clear dose-response curve, but not as good as 10% $CaCl_2$ activated PPP. A commercial source of cord plasma (untreated) did not improve growth by much; $CaCl_2$ was not used to activate the cord plasma although the pattern of diminishing cell growth at higher cord plasma concentrations suggests a CPD effect.

Human dermal fibroblasts did not grow as well in 10% FBS alone or growth factor (GF) alone. However, the combination of FBS+GF had the best results with fast and most cell growth by 7 days (right side of FIG. 7). Unlike HeLa cells, human dermal fibroblasts require higher concentrations of PPP and activation by $CaCl_2$ to stimulate cell growth.

FBS+GF stimulated cell growth earlier and faster than $CaCl_2$-activated PPP. By day 3, the cell number is more than twice as much as the cultures with activated PPP. By 7 days, however, CaCl2-activated PPP cell count was catching up. Growth factors stimulate growth immediately whereas exosomes take time to stimulate the cells to produce growth factors.

Activated PPP and PDF likely stimulate growth primarily through exosomes. Exosomes need time to stimulate the cultured cells to make their own growth factor and thus the growth curve may lag behind by several days. If freeze-dried platelets were used to supplement the cell growth at the beginning, this early growth difference could be minimized.

Confirming Studies of $CaCl_2$ Activated PPP on Cell Growth:

$CaCl_2$-activated PDP was tested on a variety of cells, including HeLa cells, Hep cells (human hepatocytes) NHDF cells (normal human dermal fibroblasts) and MIHA cells (immortalized human hepatocyte cell line). Hela cells grown for 4 days in 1% and 5% PPP had similar cell counts compared to cells cultured in 10% FBS and 10% human serum (HS), meaning that 1% and 5% PPP are as good as 10% FBS and 10% HS. Likewise, Hela cells grown for 7 days in 1%, 2.5%, and 5% PRP had similar counts to or exceeded those of 10% FBS. Hep cells grew in 1% PPP as well as 1% FBS. NHDF grew 10× more cells in 10% PPP than 10% cord plasma (commercial). NHDF grows MIHA grows as well in 1% FBS as 1% PPP.

Example 5

Novel Efficient Exosome Isolation Methods

Described herein are novel and efficient methods for isolating exosomes from UCB PDP by adding PEG (molecular weight 10,000). Exosomes in UCB plasma are soluble because water molecules bind to proteins on the exosome surface lipid membrane. If less water binds to the exosomes, the exosomes are less soluble in water and prefer to be in hydrophobic PEG. PEG is partly soluble in water. When PEG is added to water or phosphate-buffered saline and the mixture is then agitated, PEG forms bubbles. If the bubbles are bigger than (have a diameter above) the wavelength of visible light, the PEG bubbles can be seen with the eye and the solution will appear cloudy. However, if they are smaller than the wavelength of visible light, the solution is transparent and clear to the eye. Ultrasonication of the PEG solution creates microbubbles <380 nanometers in diameter. The visible light spectrum starts at 380 to 700 nanometers. The ultrasonicated solution becomes transparent to the eye.

Lower temperatures reduces the solubility of exosomes in aqueous solutions and increase the preference of exosomes for PEG. At lower temperatures close to freezing (e.g., 4° C.), water molecules detach from the surface of exosomes to join ice that is beginning to form. When this happens, the exosomes will become less soluble in water and preferentially partition into the PEG bubbles. Ultrasonication of the PEG before adding the exosome-containing plasma breaks up the PEG bubbles into smaller bubbles to less than 380 nanometers diameter. This clears the solution so that the cloudiness disappears. At 4° C., about 50% of the plasma exosomes partition into the PEG microbubbles over the period of approximately an hour. The optimum final concentration of ultrasonicated PEG solution for extracting exosomes is about 10%. If the plasma and PEG are then kept overnight at 4° C., 90-95% of the exosomes partition into the PEG.

The method described above can collected as much as $10^{12}$ exosome size particles (30-150 nm) per 10 ml of UCB plasma. This is over 100 times the $10^{10}$ exosomes collectable from 10 ml of peripheral blood serum and over 100 times more than $10^{10}$ exosomes collected from 10 ml of cell culture media. This has several implications. First, 10% PEG is more than enough to collect 90-95% of $10^{12}$ exosomes from 10 ml of cord blood plasma. Second, if the PEG suspension is not ultrasonicated or kept at 4° C., less than 20% of the exosomes will partition into the PEG. Ultrasonication greatly increases the surface area of the PEG microbubbles, allowing more interactions between exosomes and PEG microbubbles. At 4° C., the solubility of exosomes decreases and therefore are more likely to move into the PEG.

Centrifugation (2500×g) of the plasma and ultrasonicated PEG solution will form a PEG pellet at the bottom of the tube, containing >90% of the exosomes. If higher molecular weight PEG is used, i.e., 10,000 molecular weight, the PEG is heavier than water and will settle to the bottom of the tube after 30 minutes of centrifugation at 3000×g. By using 10,000 molecular weight PEG and overnight (e.g., 8 hours) incubation of the plasma and the PEG solution, extraction of 95% or more of exosomes from UCB plasma was achieved. Though commercial kits of PEG are being sold for isolating exosomes, these kits typically isolate only 20% of exosomes from blood and plasma, as well as conditioned culture media. The novel methods described herein not only isolate >90% of exosomes from UCB plasma but also from culture media and adult peripheral blood plasma.

serum collected by the P/PEG method. The particle count ranges from $6 \times 10^{10}$ (60 billion) in saliva to $2.5 \times 10^9$ (2.5 billion) in conditioned media from human liver cell cultures.

TABLE 2

Particle counts, recovery rate, and distribution of particle size collected with ultrasonicated PEG (molecular weight 10,000) 20% PEG concentration in phosphate buffered saline. PDP = platelet depleted plasma. PEG (2 h) refers to incubation at 4° C. for 2 hours before centrifugation, PEG (8 h) refers to incubation overnight at 4° C. for 8 hours. D/10 is the lower 10% of particle size, D/50 is the 50th percentile of particle diameter, D/90 is the 90th % percentile of particle diameter. Recovery is the ratio of the total count of PEG (8 h) count divided by the total count of PDP.

| Sample | Count/ml | Total count | Recovery | D/10 nm | D/50 nm | D/90 nm |
|---|---|---|---|---|---|---|
| PDP | $8.2 \cdot 10^{10}$ | $8.2 \cdot 10^{11}$ | | 90.6 | 112.4 | 171.0 |
| PEG (2 h) | $8.0 \cdot 10^{11}$ | $4.0 \cdot 10^{11}$ | 48.7% | 69.5 | 92.4 | 124.8 |
| PEG (8 h) | $1.5 \cdot 10^{12}$ | $7.5 \cdot 10^{11}$ | 91.0% | 67.9 | 99.0 | 135.8 |

In summary, some embodiments of a method of isolating exosomes include incubating ultrasonicated 10,000 molecular weight PEG (10% concentration) with PDP overnight (8-hour) at 4° C. to extract >90% of exosomes from plasma into the PEG. Centrifugation at 3000×g for 30 minutes creates a PEG pellet containing >90% of the exosomes. Because PEG is a cryopreservant, the PEG pellet can be directly frozen at −80° C. or −180° C.

A typical protocol for extracting or isolating exosomes from PDP

Equipment and Reagents:

Ultrasonicator (Fisherbrand™ Model 705 Sonic Dismembrator or equivalent)

Refrigerated centrifuge with a swinging bucket rotor

PEG (10 kD, Sigma Cat #81280-1 Kg)

0.22 μm filter system (Corning Cat #430767 or equivalent)

0.1 μm filter system (Nalgene Cat #565-0010 or equivalent)

50 ml conical tube (BD Falcon 352098 or equivalent)

Saline filtered through 0.1 μm filter unit

Starting Material

Frozen Human UCB PDP or Fresh Human UCB PDP

Procedure

A—PEG Stock Solution:

Prepare 50% (w/v) of PEG in deionized water

Sonicate the PEG solution for 1 h on ice to obtain a homogeneous aqueous solution (the setting is depended on the volume and instrument recommendation.)

Centrifuge at 5,000×g for 20 min at 4° C.

Filter supernatant with a 0.22 μm filter unit and store at room temperature

B—Exosome Isolation:

1. Thaw HUCBPDP on ice, or at 4° C. overnight.

2. Filter PDP with a micropore (0.22 μm) filter.

3. Mix the filtered PDP with an appropriate amount of PEG stock solution to a final concentration in the mixture (which has final 10% PEG concentration).

4. Incubate at 4° C. overnight (no agitation needed)

5. Centrifuge at 3,000×g for 30 min at 4° C.

6. Aspirate and save the supernatant (Exosome Depleted Plasma (EDP)).

7. Resuspend exosome pellet in Saline with ⅒th of the PDP volume using a stir bar to dissolve the pellet.

8. Aliquot and freeze at −80° C.

Biological fluids contain billions of exosomes per ml. Depending on the methods used, the numbers of particles range from $2.5 \times 10^9$ (2.5 billion) to $2.0 \times 10^{10}$ (20 billion) in The PDP was filtered with a micropore filter to eliminate large extracellular vesicles and debris. The distribution of particle diameters in PDP has a lower 10th percentile (D/10) of 90.6 nm and a higher 90th percentile (D/90) of 171.0 nm. Once the particles partition into the PEG, D/10 falls to 69.5 nm and D/90 falls to 124.8 nm after being incubated for 2 hours at 4° C. After 8 hours of incubation at 4° C., D10 is 67.9 nm and D90 is 135.8 nm. The counts suggest that an order of magnitude more exosomes are being collected than published reports. The particle count per ml for PDP is $8.2 \times 10^{10}$ or 82 billion/ml. The total count is 820 billion/10 ml. After incubation with 20% PEG and then counted from samples of the PEG pellet, the concentration increases to $8.0 \times 10^{11}$/ml or 800 billon/ml of the PEG pellet. The pellet contained 48.7% of the exosomes in the PDP. After incubation for 8 hours, the number of particles nearly doubled, suggesting a 91% recovery of exosomes.

The microbubbles may play a role in limiting the size of exosomes that could partition into the PEG. Extracellular vesicles that exceed 150 nm in diameter. The filtering with a 0.22μ filter may eliminate all debris bigger than 0.22μ in PDP but the D/90 falls from 171.0 to 135.8 nm without further filtration. The microbubbles may exclude larger vesicles that are too big to fit. PEG microbubbles are less than the wavelength of visible light (350 nm) because ultrasonication clears cloudiness due to PEG bubbles. The total count of exosomes collected from 10 ml of PDP is 750 billion, far more than the count in the Deregibus, et al. 2016 (Int J Mol Med. 2016; 38(5):1359-66) study which exceeded 65 billion in saliva. Our informal studies of commercial exosomes kits suggest that the best of them collect 20% of the exosomes from PDP and many kits probably collect less than 10%.

Example 6

Identification of Markers in UCB Exosomes and Exosome Effects on Cell Growth

Figure 8:
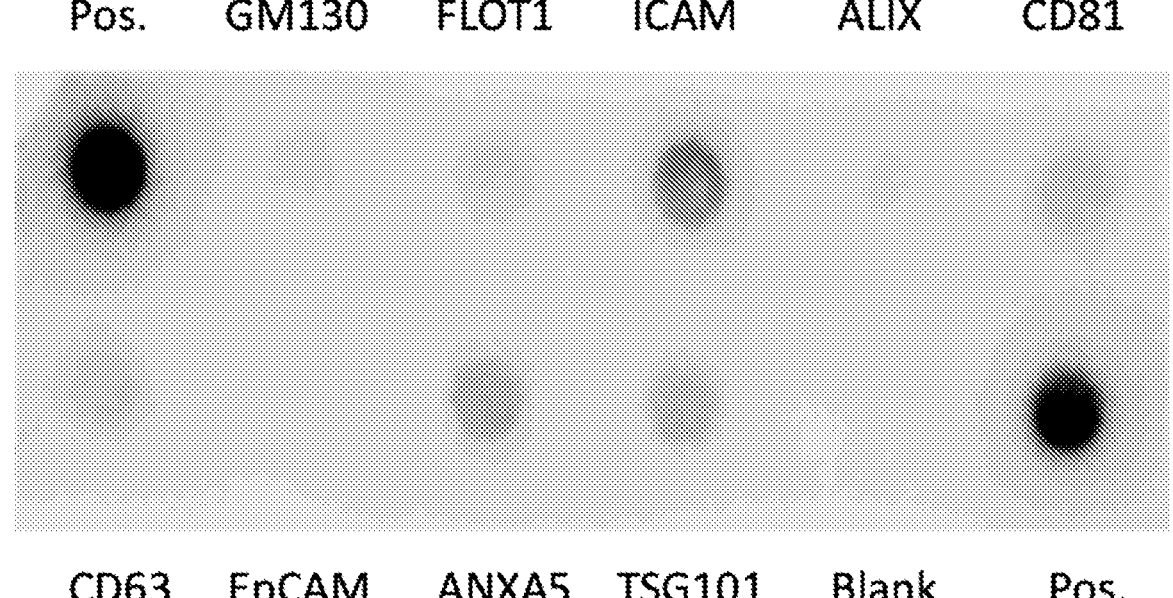
FIG. 8 is a photograph of a dot blot analysis of common markers of exosomes, applied to UCB exosomes. Positive responses include ICAM, ANXAS, TSG101, CD63, CD81, FLOT1.

Exosomes express many markers. Some of the more common exosome markers were chosen and "dot blots" were performed to determine UCB PDP exosomes markers (see FIG. 8). The most prominent marker is ICAM. The second most prominent marker is ANXAS. The fourth is CD81 or TAPA-1 (target of the antiproliferative antibody) and tetraspanin, the fifth is CD63, and the sixth is FLOT1.

Figure 9:
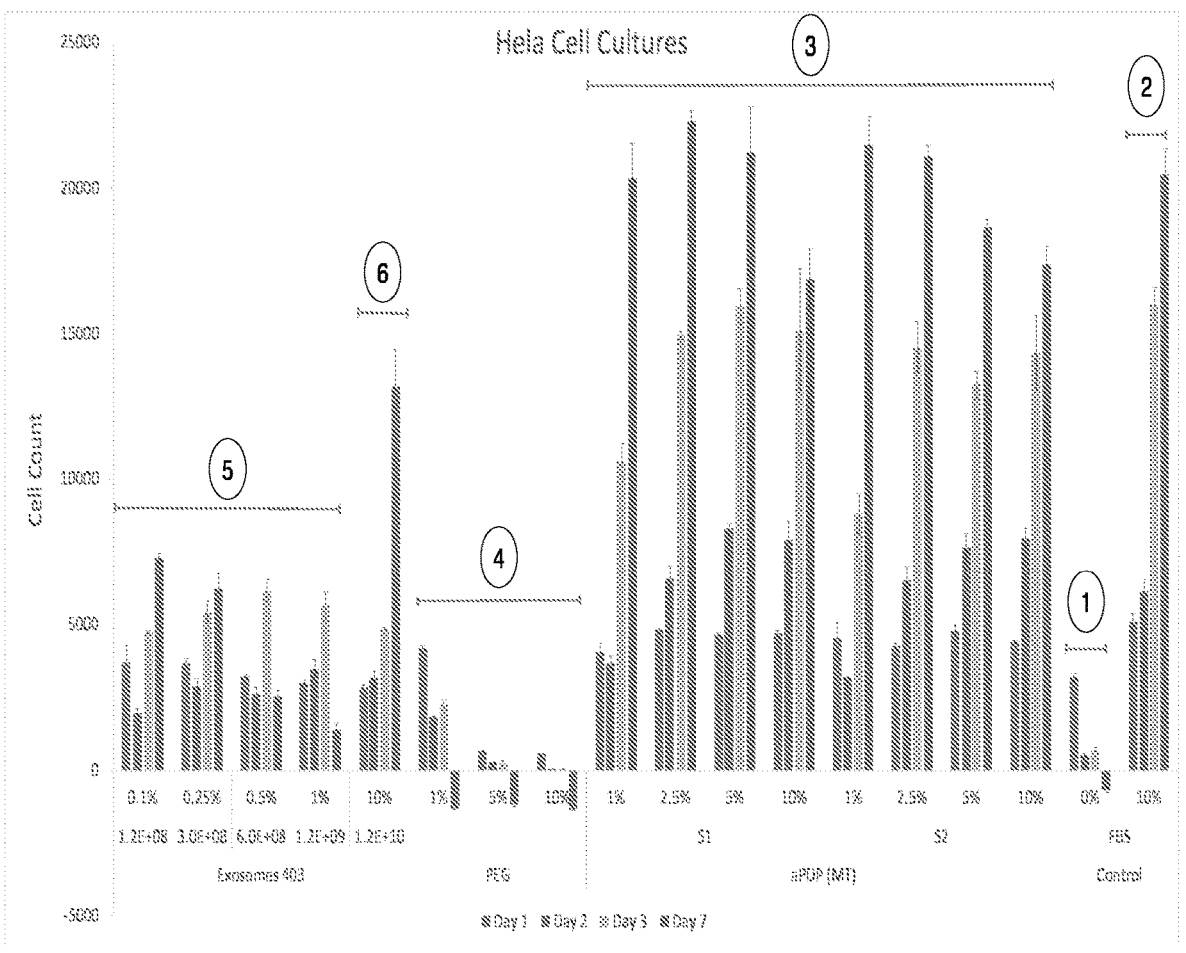
FIG. 9 is a graph showing effects of PDP and exosomes on Hela cell cultures. On the right are effects of PDP: 1%, 2.5%, 5%, and 10%) obtained from S1 and S2 cord blood plasma samples obtained from October 2017 and November 2019, stored frozen at −20° C., and then used to promote Hela cell growth. Even at 1%, aPDP remarkably stimulated Hela cell growth. On the left, application of various concentrations of exosomes, ranging from $1.2 \times 10^8$ particles to $1.2 \times 10^{10}$, stimulated Hela cell growth. PEG alone did not stimulate much growth.

UCB exosomes have significant effects on cell growth, as shown in FIG. 9. As shown, UCB exosomes supported growth of HeLa cells. The exosomes were extensively washed and did not have the any of plasma proteins. Note that PDP has exosomes already and represent the combined growth stimulatory effects of plasma proteins and exosomes. The negative control was PEG only and those cultures showed no growth. The positive controls were 1-10% PDP and 10% FBS. These data show that the exosomes collected by ultrasonicated PEG and cold extraction are active and support cell growth.

REFERENCES

Deregibus, M. C., F. Figliolini, S. D'Antico, P. M. Manzini, C. Pasquino, M. De Lena, C. Tetta, M. F. Brizzi and G. Camussi, 2016. Charge-based precipitation of extracellular vesicles. Int J Mol Med. 38, 1359-1366. 38.
Ehrhart, J., P. R. Sanberg and S. Garbuzova-Davis, 2018. Plasma derived from human umbilical cord blood: Potential cell-additive or cell-substitute therapeutic for neurodegenerative diseases. J Cell Mol Med. 22, 6157-6166. 22.
Genschmer, K. R., D. W. Russell, C. Lal, T. Szul, P. E. Bratcher, B. D. Noerager, M. Abdul Roda, X. Xu, G. Rezonzew, L. Viera, B. S. Dobosh, C. Margaroli, T. H. Abdalla, R. W. King, C. M. McNicholas, J. M. Wells, M. T. Dransfield, R. Tirouvanziam, A. Gaggar and J. E. Blalock, 2019. Activated PMN Exosomes: Pathogenic Entities Causing Matrix Destruction and Disease in the Lung. Cell. 176, 113-126 e15. 176.
Miyanishi, M., K. Tada, M. Koike, Y. Uchiyama, T. Kitamura and S. Nagata, 2007. Identification of Tim4 as a phosphatidylserine receptor. Nature. 450, 435-9. 450.
Nakai, W., T. Yoshida, D. Diez, Y. Miyatake, T. Nishibu, N. Imawaka, K. Naruse, Y. Sadamura and R. Hanayama, 2016. A novel affinity-based method for the isolation of highly purified extracellular vesicles. Sci Rep. 6, 33935. 6.

ABBREVIATIONS aPDP Activated PDP (by adding $CaCl_2$ to PDP)
$CaCl_2$ Calcium chloride
CPD Citrate-phosphate-dextrose
CPDA1 Solution of citrate-phosphate-dextrase used for UCB anticoagulation
CSF Cerebrospinal Fluid
DES Dry eye syndrome
EGF Epidermal growth factor
ERP Exosome rich plasma
EV extracellular vesicle
FBS Fetal bovine serum
FDA Food and Drug Administration (US)
FGF Fibroblast growth factor
G-CSF Granulocyte colony-stimulating factor
HeLa Henrietta Lack (a cervical carcinoma cell line that comes from this person)
HS Human serum (adult)
IFN-γ Interferon-gamma
IL-2 Interleukin-2, a cytokine that controls activities of leukocytes
IL-6 Interleukin 6 (IL-6), a pro-inflammatory cytokine
IgA Immunoglobulin A
IgG Immunoglobulin G
IgM Immunoglobulin M
IVF In vitro fertilization
mM millimolar (concentration)
mRNA messenger RNA
µRNA microRNA MNC Mononuclear cells
MVB Multivesicular bodies
NT No Treatment (group)
PDP Platelet-depleted plasma
PEG Polyethylene glycol
PPP Platelet-Poor Plasma (supernatant of centrifuged PRP)
PRP Platelet-rich-plasma
RCF Red cell fraction
PDP sample 1 collected in October 2017
S2 PDP sample 2 collected in November 2019
SCI Spinal cord injury
TNF-α Tumor necrosis factor-alpha
UCB Umbilical cord blood
VEGF Vascular endothelial growth factor

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features. From the above description, one skilled in the art can easily ascertain the essential characteristics of the present invention, and without departing from the spirit and scope thereof, can make various changes and modifications of the invention to adapt it to various usages and conditions. Thus, other embodiments are also within the scope of the following claims.

What is claimed is:

1. A method of isolating one or more of: exosomes, globulins, fibrinogen, and albumin from a tissue source, the method comprising:
   i. providing a tissue source of exosomes, globulins, fibrinogen, and albumin;
   ii. subjecting the tissue source to filtration with a micropore filter comprising pores that are 0.22 µm in diameter resulting in a plasma filtrate comprising exosomes, globulins, fibrinogen, albumin, and citrate-phosphate-dextrose (CPD);
   iii. adding the plasma filtrate to a solution comprising ultrasonicated polyethylene glycol (PEG) bubbles that are less than 340 nm in diameter and transferring the solution to a first centrifuge tube such that the exosomes partition into PEG bubbles;
   iv. cooling the first centrifuge tube to 2° C. to 8° C. for 8 hours or more;
   V. centrifuging the first centrifuge tube such that the exosomes and the PEG form a first pellet, and a first supernatant is formed, the first supernatant comprising albumin, globulins, CPD, and fibrinogen; and
   vi. recovering the first supernatant and freezing the first pellet comprising exosomes and PEG for storage;
   wherein about 80% to about 95% of the exosomes from umbilical cord blood (UCB) are isolated.

2. A method of producing exosome-rich plasma (ERP), the method comprising adding plasma or a saline solution to an exosome pellet obtained according to the method of claim 1.

3. A method for treating dry-eye syndrome, an orthopedic disorder, or a dental disorder in a subject, the method comprising administering to a subject suffering from dry-eye syndrome, an orthopedic disorder, or a dental disorder, an effective amount of the produced by the method of claim 2.

4. A method for stimulating uterine vascularization in a subject in need thereof, comprising administering to the subject's uterine cavity ERP produced by the method of claim 2.

5. A method of culturing mammalian cells, comprising: culturing a population of mammalian cells in a culture medium comprising the exosomes, globulins and/or the albumin isolated by the method of claim 1.

6. The method of claim 1, wherein the tissue source is umbilical cord blood (UCB).

7. A method for regenerating a tissue in a subject, comprising administering to the subject an effective amount of the exosomes isolated by the method of claim 1.

8. The method of claim 7, wherein the subject is a human suffering from at least one disorder selected from the group consisting of: tissue damage, brain degeneration, central nervous system degeneration, and cardiovascular degeneration.

9. A method for treating fibrinogenemia or a clotting deficiency in a subject, comprising administering to the subject suffering from fibrinogenemia or a clotting deficiency an effective amount of the fibrinogen isolated by the method of claim 1.

10. A method of culturing mammalian cells, comprising: growing a population of mammalian cells in a culture medium comprising a growth solution comprising exosomes isolated according to the method of claim 1.

11. A method for treating hypoxia, ischemia, or stroke in a subject, comprising administering to a subject suffering from hypoxia, ischemia, or stroke exosomes isolated according to the method of claim 1.

12. The method of claim 1 further comprising the following steps:

vii. mixing a precipitating agent with the first supernatant to precipitate CPD;

viii. filtering the precipitating agent and first supernatant mixture to remove the CPD resulting in a second supernatant lacking CPD;

ix. cooling the second supernatant to 2° C. to 8° C. to form a cryoprecipitate comprising fibrinogen;

X. centrifuging the cryoprecipitate in a further centrifuge tube to form a second pellet and a third supernatant, xi. removing the third supernatant which comprises albumin, and freeze-drying the cryoprecipitate comprising fibrinogen; and xii. freezing-drying the albumin-containing third supernatant.

13. The method of claim 12, wherein exosomes, fibrinogen, and albumin, are isolated.

14. The method of claim 13, wherein the precipitating agent is $CaCl_2$.

15. The method of claim 1, wherein about 90% of the exosomes from the tissue source are isolated.

16. The method of claim 1, wherein in step (iv) the first centrifuge tube is cooled under conditions such that globulins in the plasma filtrate crosslink fibrinogen, exosomes partition into PEG bubbles, and a precipitating reagent precipitates CPD.

17. The method of claim 1, wherein in step (v), the first centrifuge tube is centrifuged at a speed in the range of about 1000 to about 5000 revolutions per minute (RPM) for a time period in the range of about 5 minutes to about 30 minutes.

18. The method of claim 1, wherein the tissue source is selected from the group consisting of UCB, umbilical cord, umbilical cord lining, umbilical cord stroma cells (Wharton's jelly), amniotic fluid, amniotic membranes, placenta, and peripheral blood.

\* \* \* \* \*